(12) United States Patent
Lapeyre et al.

(10) Patent No.: US 6,395,024 B1
(45) Date of Patent: May 28, 2002

(54) MECHANICAL HEART VALVE

(75) Inventors: Didier Lapeyre, Pacy sur Eure (FR); Ulrich Steinseifer, Aachen (DE)

(73) Assignee: Triflo Medical, Inc.

( * ) Notice: Subject to any disclaimer, the term of this patent is extended or adjusted under 35 U.S.C. 154(b) by 0 days.

(21) Appl. No.: 09/323,402

(22) Filed: Jun. 1, 1999

Related U.S. Application Data

(63) Continuation-in-part of application No. 09/035,981, filed on Mar. 6, 1998, now Pat. No. 6,068,657, which is a continuation of application No. 08/859,530, filed on May 20, 1997, now abandoned.
(60) Provisional application No. 60/088,184, filed on Jun. 5, 1998.

(51) Int. Cl.$^7$ .................................................... A61F 2/06
(52) U.S. Cl. ...................................................... 623/2.22
(58) Field of Search .......................... 623/2.1, 2.2, 2.22, 623/2.23, 2.25, 2.28, 2.29, 2.33, 2.42

(56) References Cited

U.S. PATENT DOCUMENTS

| | | | | |
|---|---|---|---|---|
| 4,240,161 A | * | 12/1980 | Huffstutler, Jr. et al. ... | 623/2.23 |
| 4,425,670 A | * | 1/1984 | Figuera ...................... | 623/2.22 |
| 4,676,789 A | * | 6/1987 | Sorenson et al. .......... | 623/2.22 |
| 4,775,378 A | | 10/1988 | Knoch et al. | |
| 4,872,875 A | * | 10/1989 | Hwang ....................... | 623/2.22 |
| 4,923,465 A | | 5/1990 | Knoch et al. | |
| 5,123,918 A | | 6/1992 | Perrier et al. | |
| 5,314,467 A | * | 5/1994 | Shu ............................ | 623/2.28 |
| 5,545,216 A | | 8/1996 | Bokros et al. | |
| 5,628,791 A | | 5/1997 | Bokros et al. | |
| 5,641,324 A | | 6/1997 | Bokros et al. | |
| 5,772,694 A | | 6/1998 | Bokros et al. | |
| 5,814,100 A | | 9/1998 | Carpentier et al. | |
| 5,961,550 A | | 10/1999 | Carpentier et al. | |
| 6,039,759 A | | 3/2000 | Carpentier et al. | |
| 6,059,826 A | | 5/2000 | Bokros et al. | |
| 6,096,075 A | | 8/2000 | Bokros et al. | |

FOREIGN PATENT DOCUMENTS

| | | |
|---|---|---|
| EP | 0 220 097 | 4/1987 |
| EP | 0 383 676 | 8/1990 |
| WO | WO 85/04094 | 9/1985 |

OTHER PUBLICATIONS

International Search Report, International Application No. PCT/US99/12212, Sep. 21, 1999.

* cited by examiner

*Primary Examiner*—Eduardo C. Robert
(74) *Attorney, Agent, or Firm*—Morgan, Lewis & Bockius LLP

(57) ABSTRACT

An improved trileaflet mechanical heart valve 100 can include an improved leaflet 110. The valve 100 and leaflet 110 provide improved flow characteristics, minimize blood clotting behind the leaflets, and provide more natural opening and closing times. The valve can include a valve housing 105 which contains pivot/hinge mechanism (130, 200, and 300) for allowing rotation of and retention of the leaflets 110. The valve housing 105 can also include windows or openings 125 which allows for complete washing of the pivot/hinge mechanism (130, 200, and 300) as well as the leaflets 110. The novel leaflets 110 are airfoil-like having a complex S-shaped curvature on their outer surface. This novel geometry, when combined with the location of the leaflet's pivot axis, causes a tendency for the leaflets 110 to rotate towards the closed position. Thus, the leaflets 110 begin to close much earlier than a conventional leaflet and are substantially closed before the flow reverses, similar to the function of a natural valve.

59 Claims, 18 Drawing Sheets

MECHANICAL HEART VALVE

CONTINUING DATA

This application claims priority under 35 U.S.C. §119(e) to U.S. Provisional Application No. 60/088,184, filed Jun. 5, 1998, and is a continuation in-part of U.S. Ser. No. 09/035,981 entitled MECHANICAL VALVE PROSTHESIS WITH OPTIMIZED CLOSING MODE, filed Mar. 6, 1998, now Pat. No. 6,068,657, whose disclosure is expressly incorporated by reference herein, and which is a continuation to its parent application, U.S. Ser. No. 08/859,530, filed May 20, 1997, now abandoned.

BACKGROUND OF THE INVENTION

FIELD OF INVENTION

The present invention relates to an improved trileaflet mechanical heart valve. More specifically, the present invention relates to a trileaflet mechanical heart valve with improved flow characteristics. Such a mechanical heart valve is useful for surgical implantation into a patient as a replacement for a damaged or diseased heart valve.

BACKGROUND CONSIDERATIONS

There are numerous considerations in the design and manufacture of a mechanical prosthetic heart valve. An important consideration is the biocompatibility of the materials used in the prosthesis. The materials used must be compatible with the body and the blood. Furthermore, the materials must be inert with respect to natural coagulation processes of the blood, i.e., they must not induce thrombosis (an aggregation of blood factors, primarily platelets and fibrin with entrapment of cellular elements, frequently causing vascular obstruction at the point of its formation) when contacted by the blood flow. A local thrombus can give rise to an embolism (the sudden blocking of a blood carrying vessel) and can even under certain circumstances hinder proper valve operation. Numerous materials have been tested for such desirable biocompatibility. Several materials are commonly used for making commercially available prosthetic heart valves (materials such as stainless steel, chromium alloys, titanium and its alloys, and pyrolytic carbon).

Another consideration in the design and manufacture of a mechanical prosthetic heart valve is the valve's ability to provide optimum fluid flow performance. Mechanical prosthetic heart valves often create zones of turbulent flow, eddies, and zones of stagnation. All of these phenomena can also give rise to thrombosis and thrombo-embolisms. Biological valves (or bioprostheses) emulate the form and the flow pattern of the natural heart valve and thus have better fluid flow performance over conventional mechanical prostheses. Such bioprosthetic valves do not require long-term anti-coagulant medication to be taken by the patient after implantation at least in the aortic position. These two thrombus-generating factors (materials used and flow characteristics) are problematic in conventional mechanical heart valve prostheses. Thus, patients who currently receive a mechanical heart valve prosthesis require a continuous regime of anti-coagulant drugs which can result in bleeding problems. The use of anti-coagulant drugs therefore constitutes a major drawback of mechanical heart valve prostheses when compared with bioprostheses.

However, biological replacement valves suffer from problems too. As clinical experience has indicated, unlike mechanical valves, their life-span of is often too short. Because of the progressive deterioration of bioprostheses, they often need to be replaced via costly additional major surgery.

Yet another consideration in the design and manufacture of a mechanical prosthetic heart valve concerns the head loss (pressure drop) associated with the valve. This head loss occurs during the systolic ejection or diastolic filling of a ventricle. In conventional designs, some head loss is inevitable since it is inherent to the reduction in the effective orifice area of the mechanical prosthetic heart valve as compared to natural valves. The reduction in effective orifice is caused by the sewing ring which is conventionally required for surgical installation of the prosthetic valve, by the thickness of the valve housing, and by the hinges which enable the valve's flaps (leaflets) to move between an open and closed position. Another portion of the head loss is due to the geometric disposition of the valve's flaps with respect to the flow of blood.

As mentioned above with respect to the progressive deterioration of bioprostheses, durability is another consideration in the design and manufacture of a mechanical prosthetic heart valve. A mechanical prosthetic heart valve should demonstrate a mechanical lifetime equivalent to approximately 380–600 million cycles (i.e., the equivalent of about 15 years). Obviously, the mechanical lifetime is related to the geometrical design of the valve as well as the mechanical characteristics of the materials used.

Of course, the valve's ability to minimize leakage is also important. Leakage generally comprises regurgitation (backward flow of blood through the valve during operation, and otherwise known as dynamic leakage) and static leakage (any flow through the valve in the fully closed position). In the conventional valves, the amount of regurgitation is at least 5% of the volume of blood flow during each cycle, and is often more. When a patient has two prosthetic valves on the same ventricle, regurgitation (dynamic leakage) thus comprises at least about 10% (leakage on the order of several hundred L per day). Thus, dynamic leakage clearly puts undesirable stress on the heart muscle. Static leakage, on the other hand, is typically caused by the imperfect mechanical sealing of the prosthetic valve when its flaps are closed. Because static leakage also causes the heart muscle to work harder, it must be taken into consideration in the design and manufacture of a mechanical prosthetic heart valve.

The closing mechanism of natural cardiac valves has not been taken into account in the design of conventional mechanical valve prostheses. When the flow rate across the valve becomes zero, the natural aortic valve is already more than 90% closed. In contrast, conventional mechanical valve prostheses at that same time remain almost fully open. From this almost fully open position, conventional mechanical valve leaflets abruptly close with the large amount of regurgitation. In an aortic position, this occurs at the very beginning of the diastole, and in the mitral position, this occurs even more abruptly at the very beginning of the systole. In conventional mechanical leaflets, the mean closing velocity of some portions of the leaflets (at 70 beats per minute) is on the order of 1.2–1.5 m/sec, whereas the highest closing velocity in a natural valve is 0.60 m/sec. Rapid angular closing speeds create cavitation in mechanical prosthetic heart valves. This high closure speed increases the intensity of the impact of the leaflets upon closure and thus, generates sufficiently large acoustical vibrations to cause discomfort in the patient, damage the blood (embolisms), and generates micro-bubble formations in the blood which may be detected by a transcranial doppler (HITS—High Intensity Transcranial Signals).

Thus, conventional mechanical heart valves suffer from several disadvantages. First, conventional mechanical heart valves fail to provide optimal blood flow characteristics. Next, conventional mechanical heart valves allow blood to stagnate behind the valve leaflets, thus creating the possibility of blood clotting in those locations. Also, conventional mechanical heart valves may not provide optimum opening and closing times (e.g., times which properly emulate a natural human valve). It has not been possible, in the past, to reproduce the flow characteristics of a natural valve when using a mechanical prosthesis. Thus, with the use of conventional mechanical heart valves, embolic incidents and subsequent mortality may be directly or indirectly linked to the valve prosthesis.

Accordingly, there is a need for an improved mechanical heart valve for implantation into a patient which provides improved flow characteristics, minimizes blood clotting behind the leaflets, and provides more natural opening and closing behavior.

SUMMARY OF THE INVENTION

Accordingly, the present invention is directed to an improved mechanical heart valve for surgical implantation into a patient which substantially eliminates one or more of the problems or disadvantages found in the prior art.

An object of the present invention is to provide for an improved mechanical heart valve for surgical implantation into a patient which provides improved flow characteristics.

Another object of the present invention is to provide for an improved mechanical heart valve for surgical implantation into a patient which minimizes the potential for blood clotting behind the leaflets.

Another object of the present invention is to provide for an improved mechanical heart valve for implantation into a patient which provides improved (e.g., more natural) opening and closing behavior.

Another object of the present invention is to provide for an improved mechanical heart valve for implantation into a patient which provides reduced regurgitation and closure volume to thereby reduce the workload on the heart.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, an exemplary embodiment relates to a rotatable leaflet for a prosthetic heart valve which includes a main portion having leading and trailing edge surfaces, and inner and outer surfaces connecting the leading and trailing edge surfaces, wherein the inner surface generally defines a convex curvature from the leading edge surface to the trailing edge surface and the outer surface generally defines a convex curvature proximate the leading edge surface and a concave curvature proximate the. trailing edge surface, and first and second winglet portions situated on opposite ends of the leaflet to facilitate pivoting or rotation of the leaflet as it opens and closes.

Another exemplary embodiment relates to a rotatable leaflet for an early-closing prosthetic heart valve including a main portion having leading and trailing edge surfaces, and inner and outer surfaces connecting the leading and trailing edge surfaces, wherein the inner surface generally defines a convex curvature from the leading edge surface to the trailing edge surface and the outer surface generally defines a convex curvature proximate the leading edge surface and a concave curvature proximate the trailing edge surface. First and second winglet portions are situated on opposite ends of the leaflet to facilitate rotation of the leaflet, and closure means is included for causing the leaflet to rotate toward a closed position prior to substantial back flow of blood through the heart valve.

Yet a further exemplary embodiment relates to mechanical prosthetic heart valve, the valve including an annular housing having an inner circumferential surface and at least one leaflet disposed adjacent to the inner circumferential surface and capable of rotation between an open position in which blood can flow through the heart valve and a closed position in which blood is prevented from flowing through the heart valve. The leaflet includes a main portion having leading and trailing edge surfaces and inner and outer surfaces connecting the leading and trailing edge surfaces, wherein the inner surface generally defines a convex curvature from the leading edge surface to the trailing edge surface and the outer surface generally defines a convex curvature proximate the leading edge surface and a concave curvature proximate the trailing edge surface. First and second winglet portions are situated on opposite ends of the leaflet to facilitate rotation of the leaflet.

Another exemplary embodiment relates to a mechanical early-closing prosthetic heart valve, the valve including an annular housing having an inner circumferential surface and at least one leaflet disposed adjacent to the inner circumferential surface and capable of rotation between an open position in which blood can flow through the heart valve and a closed position in which blood is prevented from flowing through the heart valve. The leaflet has closure means for causing the leaflet to rotate toward a closed position prior to substantial back flow of blood through the heart valve.

A further exemplary embodiment relates to a mechanical prosthetic heart valve including an annular housing having an inner circumferential surface and at least one leaflet disposed adjacent to the inner circumferential surface and capable of rotation between an open position in which blood can flow through the heart valve and a closed position in which blood is prevented from flowing through the heart valve. The leaflet includes a main portion having leading and trailing edge surfaces and inner and outer surfaces connecting the leading and trailing edge surfaces, and first and second winglet portions situated on opposite ends of the leaflet to facilitate rotation of the leaflet, and first and second leaflet pivot structures adapted to cooperate with the first and second winglets, respectively, to facilitate rotation of the at least one leaflet between the open and closed positions. Each of the first and second leaflet pivot structures includes an inflow projection extending from the inner circumferential surface of the housing and adapted to contact one of the winglet portions in the open and closed positions, and a closing projection extending from the inner circumferential surface of the housing and adapted to contact one of the winglet portions in the closed position, wherein the closing projection and the inflow projection are configured and spaced from one another to increase flow velocity proximate the one of the winglet portions.

Still another exemplary embodiment relates to a mechanical prosthetic heart valve including an annular housing having an inner circumferential surface and defining at least one opening through the annular housing, and at least one leaflet disposed adjacent to the inner circumferential surface and capable of rotation between an open position in which blood can flow through the heart valve and a closed position in which blood is prevented from flowing through the heart valve. The leaflet includes a main portion and first and second winglet portions situated on opposite ends of the leaflet to facilitate rotation of the leaflet, wherein no portion of the at least one leaflet is received within the at least one opening during rotation between the open and the closed position to provide for increased blood flow proximate to one of the winglet portions.

Still a further exemplary embodiment relates to a mechanical early-closing prosthetic heart valve, the valve including an annular housing having an inner circumferential surface, and at least one leaflet disposed adjacent to the inner circumferential surface and capable of rotation between an open position in which blood can flow through the heart valve and a closed position in which blood is prevented from flowing through the heart valve. The leaflet includes an early-closure means for creating a tendency for the leaflet to rotate toward the closed position such that the leaflet is substantially closed prior to the initiation of back flow of blood through the heart valve.

A final exemplary embodiment relates to a mechanical early-closing prosthetic heart valve, the valve including an annular housing having an inner circumferential surface, and at least one leaflet disposed adjacent to the inner circumferential surface and capable of rotation between an open position in which blood can flow through the heart valve and a closed position in which blood is prevented from flowing through the heart valve. The leaflet includes surfaces with complex curvatures for creating a tendency for the leaflet to rotate toward the closed position such that the leaflet is substantially closed prior to the initiation of back flow of blood through the heart valve.

It is to be understood that both the general description above, and the following detailed description are exemplary and explanatory and are intended to provide further explanation of the invention as claimed.

BRIEF DESCRIPTION OF THE DRAWINGS

The accompanying drawings which are included to provide a further understanding of the invention and constitute a part of this specification, illustrate embodiments of the invention and together with the written description, serve to explain the principles of the invention. In the drawings.

DETAILED DESCRIPTION OF THE PREFERRED EMBODIMENTS

Reference will now be made in detail to the preferred embodiments of the present invention, examples of which are illustrated in the accompanying drawings. For example, FIG. 1 shows an elevated isometric view of a preferred embodiment of a multi-leaflet mechanical heart valve according to the present invention with the leaflets in the fully open position so that blood can flow through the heart valve.

Figure 1:
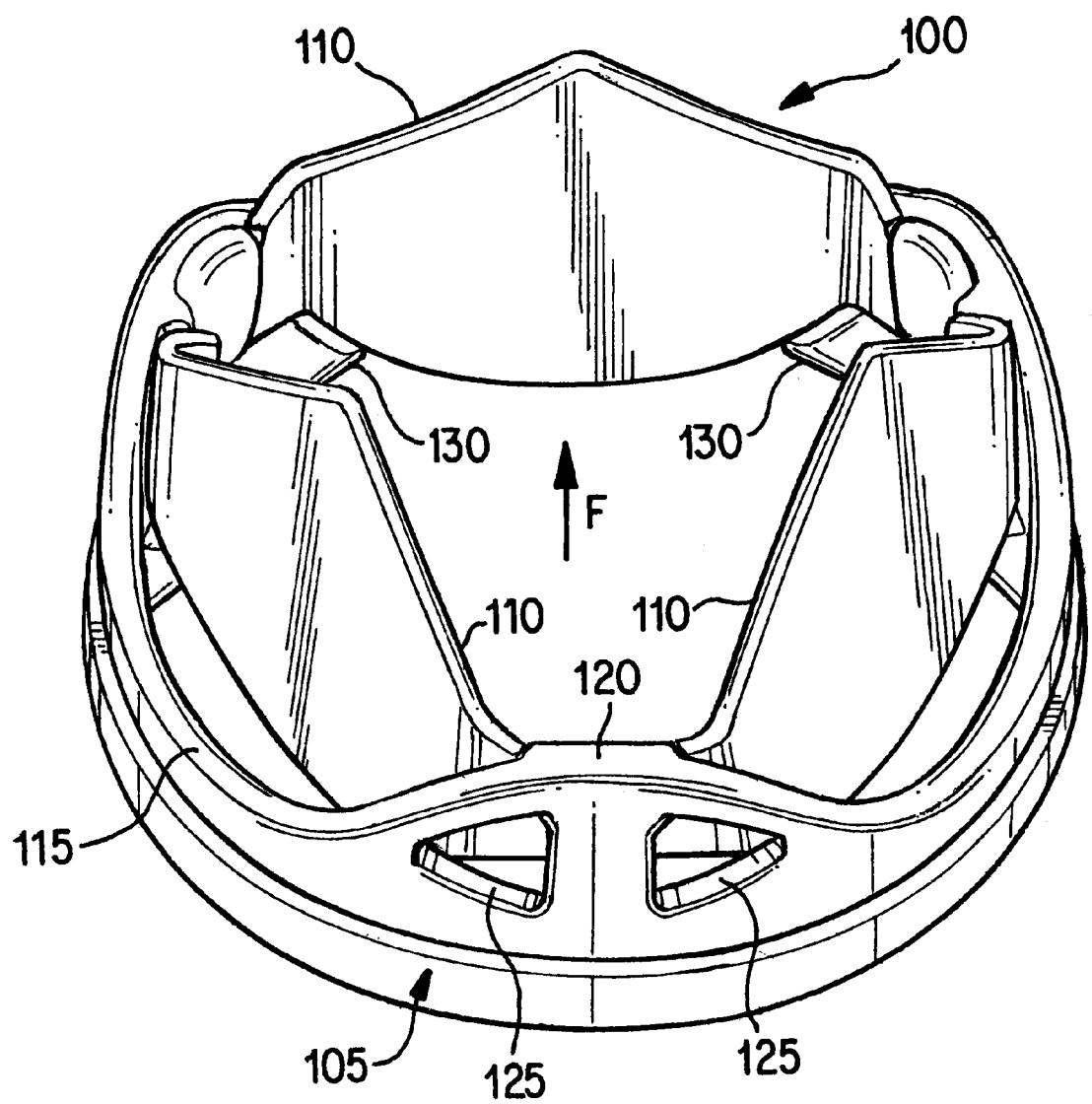
FIG. 1 is an elevated isometric view of a preferred embodiment of a multi-leaflet mechanical heart valve according to the present invention with the leaflets in the fully open position.

As illustrated in FIG. 1, the multi-leaflet mechanical heart valve 100 generally includes an annular housing 105 and rotatable leaflets 110 (as used herein, the term annular is taken to encompass any continuous surface). The housing 105 includes inner and outer circumferential surfaces, as detailed below (as used herein, the phrase circumferential surface is taken to mean the boundary surface of any closed shape). The housing 105 has three concave portions 115 and three convex portions 120 around its top surface, as well as six openings therein (called windows herein) 125 and six inflow projections 130. Note that the inflow projections 130 extend from the inner circumferential surface of the housing 105 into the blood flow path F.

Housing 105 may be constructed of any rigid biocompatible material. For example, housing 105 may be constructed from any biocompatible metallic material, such as chromium, nickel-tungsten, and titanium. Housing 105 may also be constructed of any rigid biocompatible organic material such as, for example, pyrolytic carbon. Furthermore, housing 105 may be constructed from any biocompatible polymeric material, such as a biocompatible plastic material. In the preferred embodiment, housing 105 is machined from a solid metallic rod.

Like housing 105, the leaflets 110 may be constructed of any rigid biocompatible material (metallic, organic, or polymeric). In the preferred embodiment, leaflets 110 are preferably fabricated from pyrolytic carbon. The leaflets 110 of the preferred embodiment have two complex curved, non-parallel surfaces.

Figure 2:
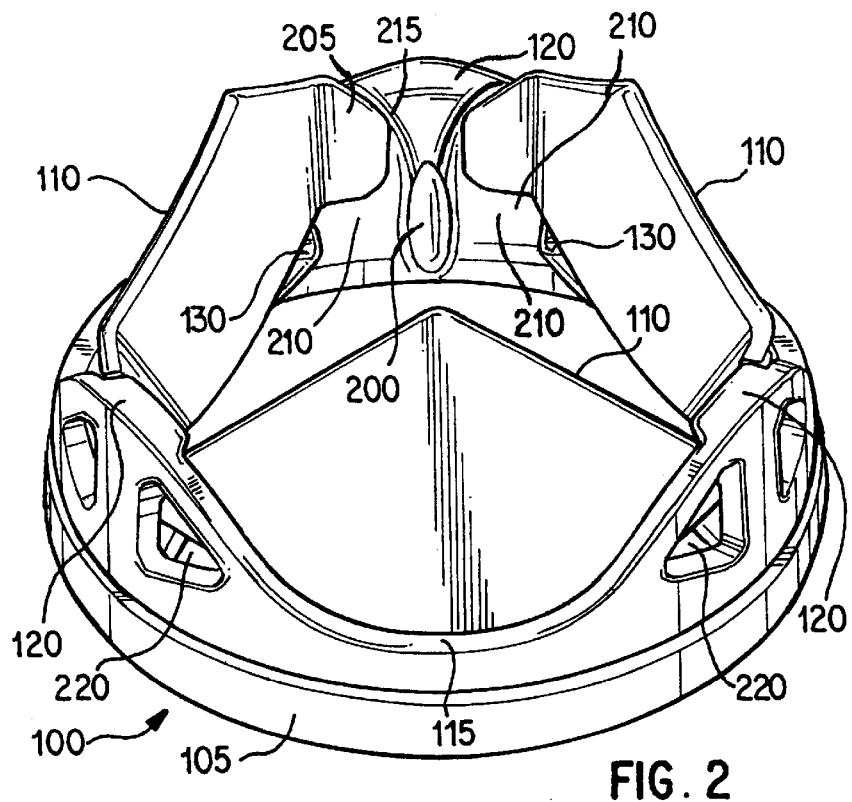
FIG. 2 is another elevated isometric view of a preferred embodiment of a multi-leaflet mechanical heart valve according to the present invention with the leaflets in an open position.

FIG. 2 shows an elevated isometric view of a preferred embodiment of a multi-leaflet mechanical heart valve according to the present invention with the leaflets 110 rotated to an open position. FIG. 2 also more clearly illustrates the structure on housing 105 which facilitates rotation of and retains leaflets 110. Each leaflet 110 has two winglets 205 (angled portions at the ends of each of the leaflets) with a main portion disposed therebetween. Winglets 205 rest on inflow projections 130 (at least when the leaflets are in the closed position). In addition to the six inflow projections 130, housing 105 also has three closing projections 200, six winglet guide paths 210, and six winglet guide arcs 215. The leaflet pivot structure of the heart valve of the preferred embodiment which retains the leaflets 110 and its winglets 205 within the housing 105 may be informatively compared to the structure described in U.S. Pat. No. 5,123,918 which is incorporated by reference herein. As shown in FIG. 2, windows 125 communicate with the blood flow through the heart valve 100 at regions denoted as 220.

Thus, windows 125 allow blood to flow across the back of the winglets 205 and substantially wash the leaflet pivot region in both the open and closed positions. This washing helps to greatly reduce blood stagnation behind the winglets 205, and thus reduces the likelihood of formation of a local blood clot or thrombus in this region.

Note that the windows 125 may be made any shape and size which allows for appropriate structural rigidity in the housing 105 and optimum washing flow through the windows and into the leaflet pivot region. In the preferred embodiment, windows 125 are triangular in shape.

Although housing 105 may be made in any annular shape, the housing of the preferred embodiment has three concave portions 115 and three convex portions 120 around the top surface of its circumference, i.e., a scalloped arrangement. These concave portions 115 and convex portions 120 play a special role during the surgical implantation of valve prothesis 100. During implantation, a sewing ring (see FIG. 26, for example) is attached to the outer circumference of housing 105. The surgeon then stitches through the tissue and through the sewing ring to attach the valve in its desired location. If the surgeon inadvertently places one or more of the stitches around the housing 105, when the stitches are pulled tight, the geometry of housing 105 will move the misplaced stitches towards concave portions 115 rather than convex portions 120. Thus, there is little opportunity for a suture to be looped over the convex portions 120 of the housing 105 and thereby impede the opening and closing of the leaflets 110.

Figure 3:
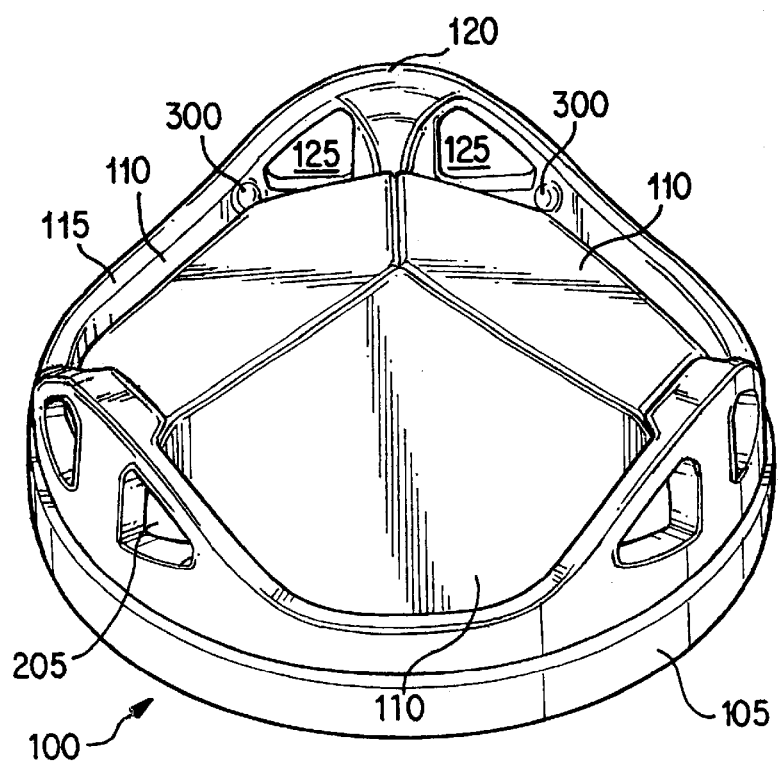
FIG. 3 is the elevated isometric view of FIG. 2 in accordance with the present invention with the leaflets in the fully closed position.

FIG. 3 an elevated isometric view of a preferred embodiment of a multi-leaflet mechanical heart valve according to the present invention with the leaflets in the fully closed position to prevent blood flow through the heart valve. As shown, housing 105 also includes six leaflet capture projections 300 which help to prevent the leaflets 110 from being easily removed from their pivot/hinge structures. The effective closing angle of the complex curved leaflet may be defined by the chord of the leaflet in its middle section. Note that in the preferred embodiment, the chord of leaflets 110 preferably close to an angle of about 30° to about 40° with respect to the inflow plane of the housing 105.

With the leaflets 110 in the closed position, the angle or pyramid shape of the closed leaflets 110 also channels the flow through the windows 125 of the valve housing 105 which results in improved washing by blood flow across the back of the winglets 205 and completely washes the leaflet pivot region. Again, this washing helps to greatly reduce blood stagnation behind the winglets 205, and thus reduces the likelihood of formation of a local blood clot or thrombus in this region.

Figure 4:
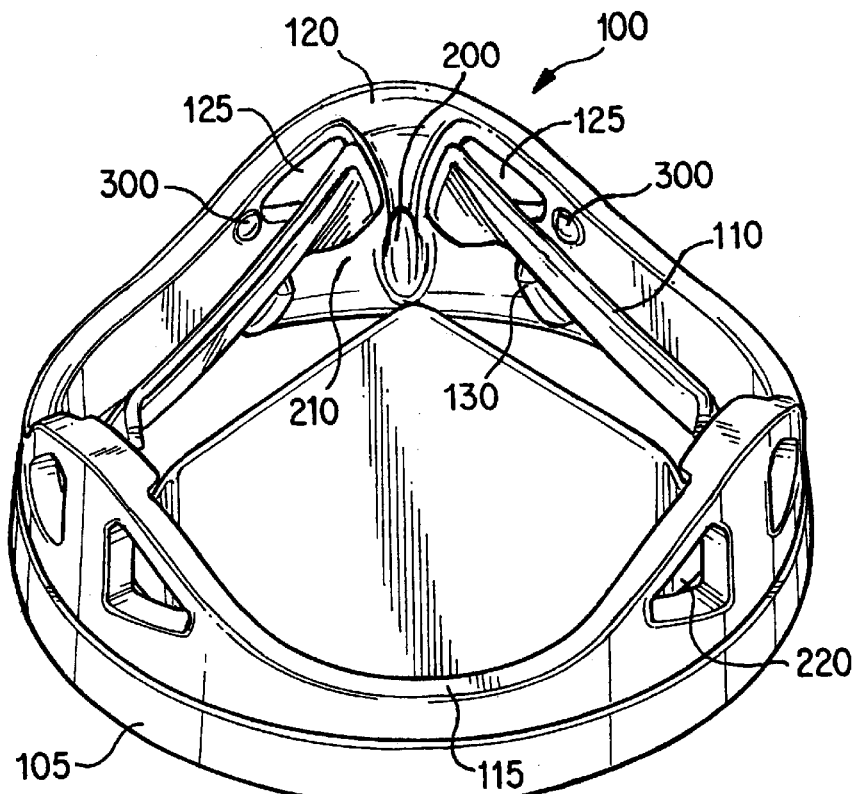
FIG. 4 is the elevated isometric view of FIG. 2 in accordance with the present invention with the leaflets in a partially open position.

FIG. 4 shows an elevated isometric view of a preferred embodiment of a multi-leaflet mechanical heart valve according to the present invention with the leaflets rotated into a partially open position (50% open—halfway between the fully open position and the fully closed position). In this position as well as any position in which the leaflets 110 are at least partially open, blood flows across the back surface of the leaflets 110 and through the windows 125 to completely wash the leaflet pivot region. As mentioned above, this washing helps to greatly reduce blood stagnation behind the winglets 205, and thus reduces the likelihood of formation of a local blood clot or thrombus in this region.

Figure 5:
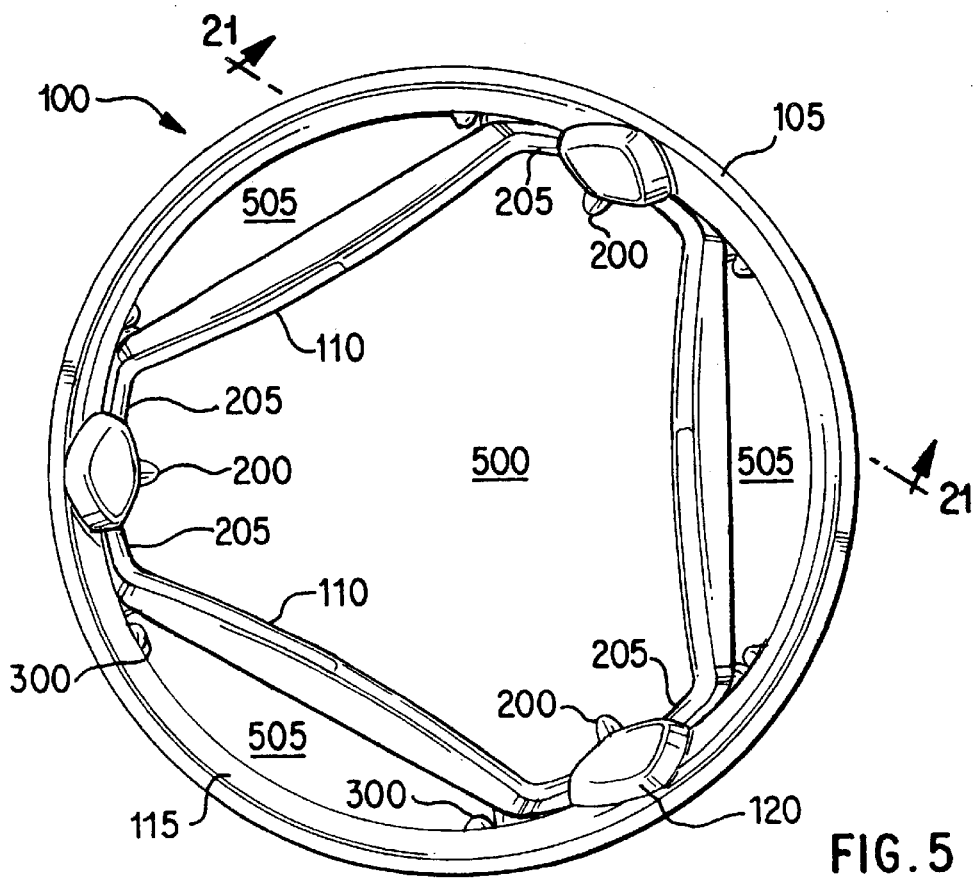
FIG. 5 is a top plan view of a preferred embodiment of a multi-leaflet mechanical heart valve according to the present invention with the leaflets in the fully open position.
Figure 8:
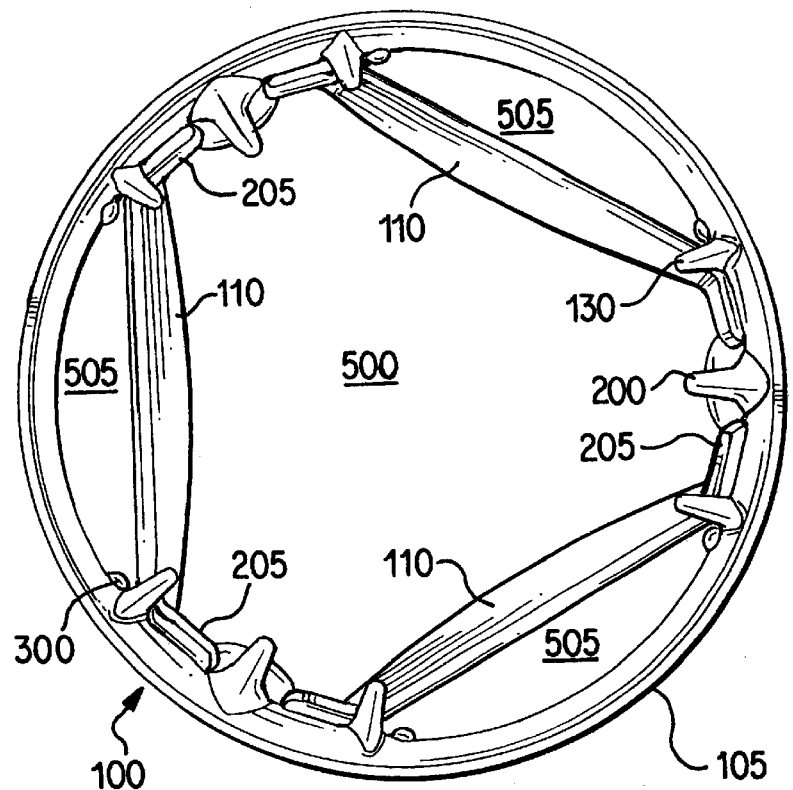
FIG. 8 is a bottom plan view of a preferred embodiment of a multi-leaflet mechanical heart valve according to the present invention with the leaflets in the fully open position.

FIG. 5 is a top plan view and FIG. 8 is a bottom plan view of a preferred embodiment of a multi-leaflet mechanical heart valve according to the present invention with the leaflets in the fully open position. As shown, the open leaflets 110 divide the blood flow through the valve 100 into several distinct flow paths. Main flow path 500 extends along the central axis of valve 100, while outer flow paths 505 are delineated by the open leaflets 110. Note, as shown in FIGS. 1 and 2, winglets 205 of leaflets 110 do not completely cover windows 125 when leaflets 110 are in the open position. Thus, in this position, as well as any open position, blood flows through windows 125 to completely wash the leaflet pivot region, reducing the possibility of stagnation or blood coagulation in this region.

Although the opening angle of the leaflets 110 may be optimized for differing requirements, the chord of the leaflets 110 of the preferred embodiment open to an effective angle of about 75° to about 90° with respect to the inflow plane of the housing 105. The effective opening angle of the complex curved leaflet may be defined by the chord of the leaflet in its middle section. This opening angle, coupled with the unique contour of the leaflets, provides for a central flow valve, similar to the natural valves of the heart. This results in a reduced pressure gradient or pressure drop across the valve in the open position when compared with most conventional mechanical heart valves.

Figure 6:
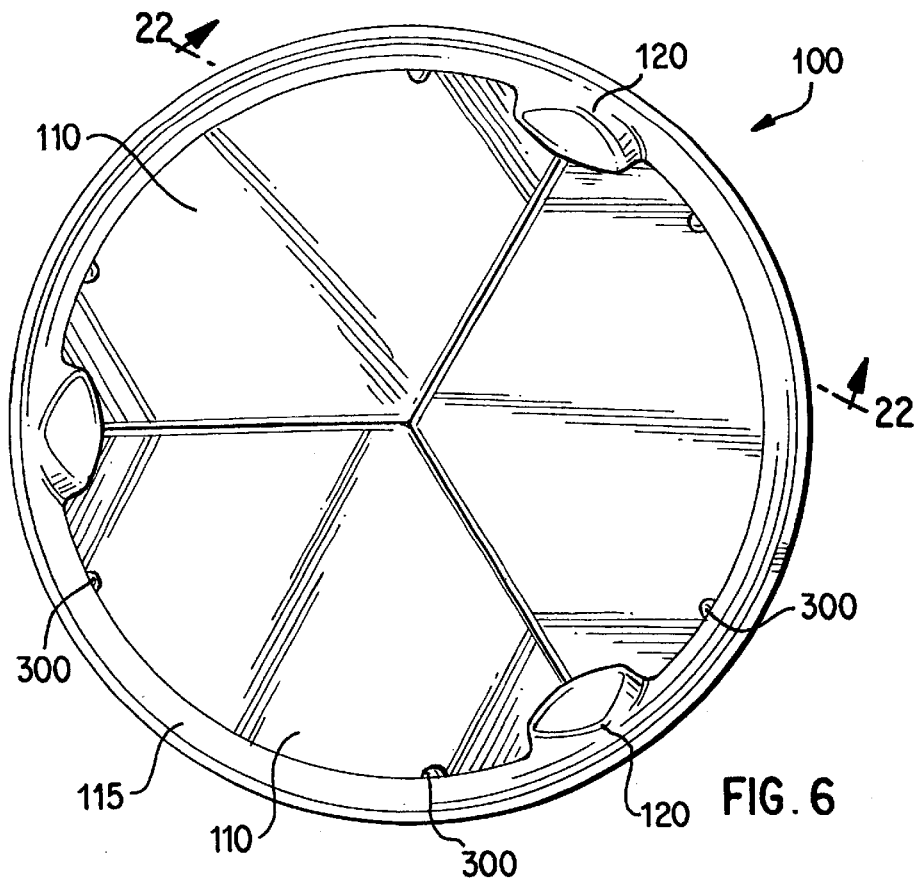
FIG. 6 is a top plan view of a preferred embodiment of a multi-leaflet mechanical heart valve according to the present invention with the leaflets in the fully closed position.
Figure 7:
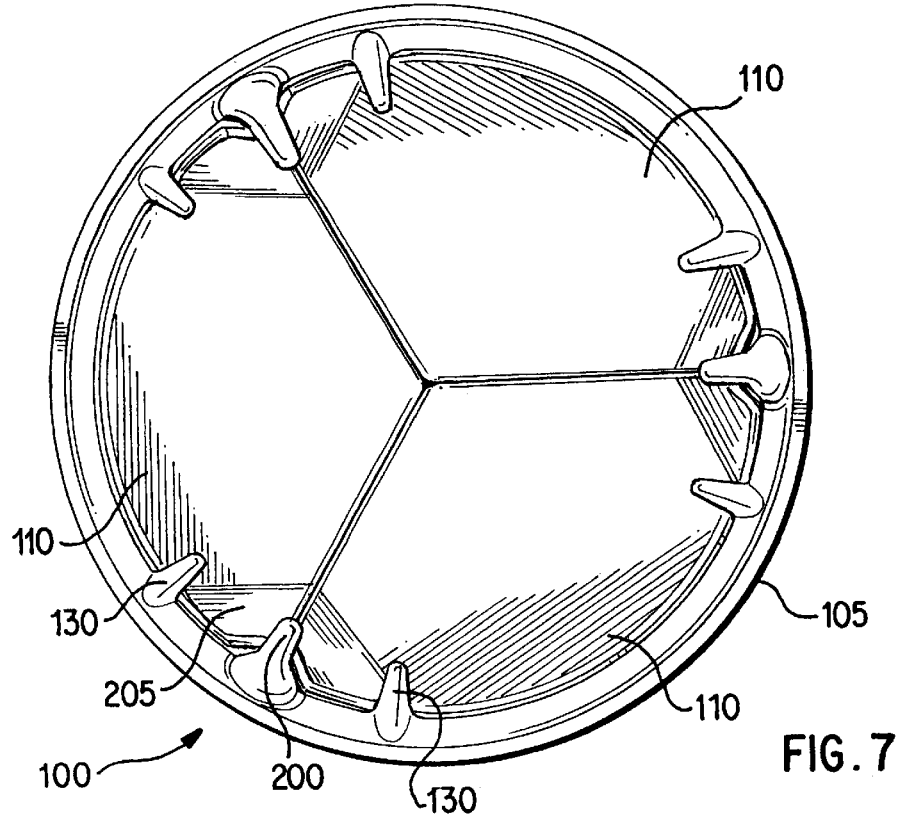
FIG. 7 is a bottom plan view of a preferred embodiment of a multi-leaflet mechanical heart valve according to the present invention with the leaflets in the fully closed position.

FIG. 6 is a top plan view and FIG. 7 is a bottom plan view of a preferred embodiment of a multi-leaflet mechanical heart valve according to the present invention with the leaflets in the fully closed position. As shown, in the preferred embodiment, the leaflets 110 close the main and outer flow paths 500 and 505 respectively. However, in some instances, it may be desirable to leave a small gap between the leaflets in the closed position. It has been discovered that a small gap, while allowing for minor static leakage, tends to improve some performance characteristics, e.g., reduces the harmful effects of cavitation (by increasing the cavitation threshold) at the trailing surfaces of the leaflets during closing. This small gap need not be continuous or constant along the intersection of the leaflets 110. It may be a gap which is widest at the pointed tips of the leaflets 110 and get progressively narrower radially towards the housing 105. It is noted that a very small opening between the leaflets only near their tips is shown in the figures (due to manufacturing).

Figure 9:
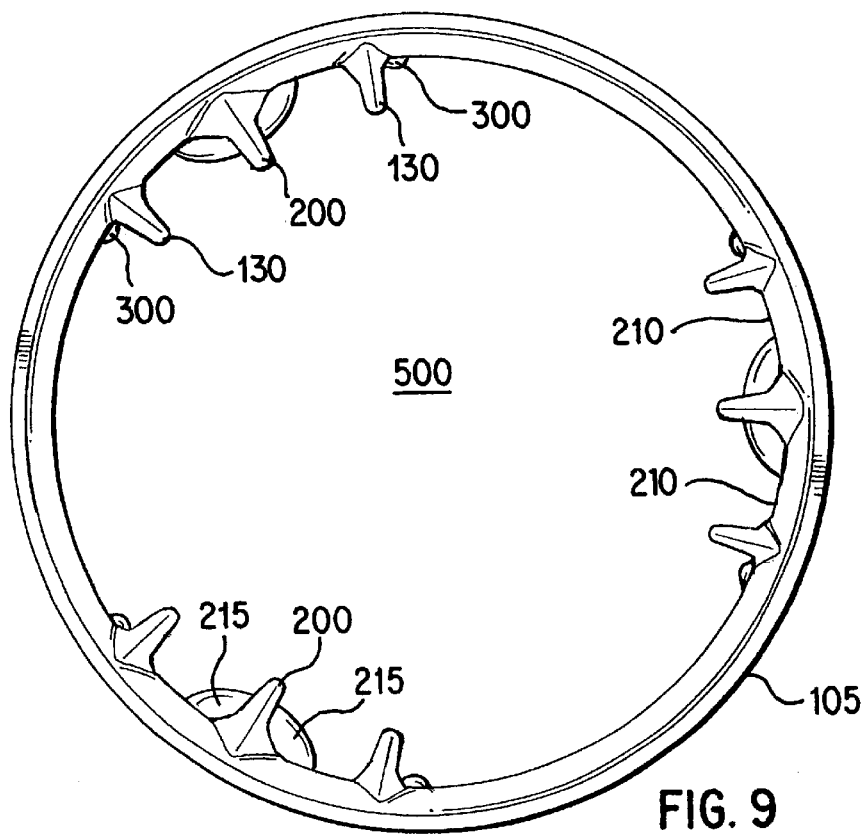
FIG. 9 is a bottom plan view of a preferred embodiment of a multi-leaflet mechanical heart valve according to the present invention with the leaflets removed.
Figure 10:
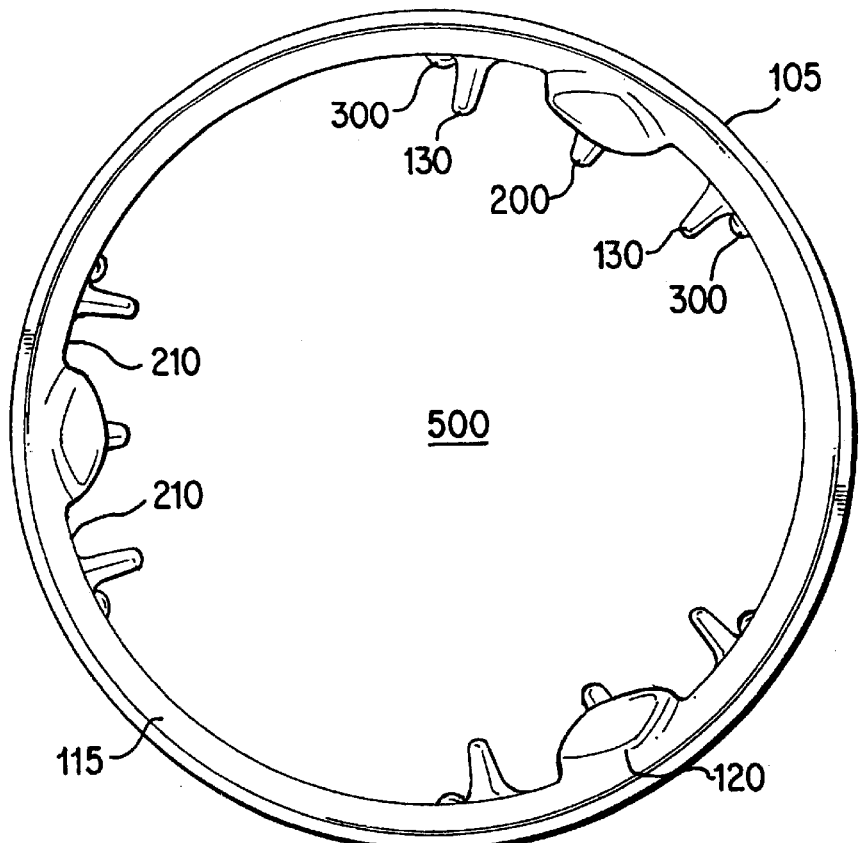
FIG. 10 is a top plan view of a preferred embodiment of a multi-leaflet mechanical heart valve according to the present invention with the leaflets removed.

FIG. 9 is a bottom plan view and FIG. 10 is a top plan view of a preferred embodiment of a multi-leaflet mechanical heart valve according to the present invention with the leaflets 110 removed. This figure illustrates the structure on housing 105 which facilitates rotation of and retains leaflets 110. As shown, this structure includes six inflow projections 130, three closing projections 200, six winglet guide paths 210, six leaflet capture projections 300, and six winglet guide arcs 215.

Figure 11:
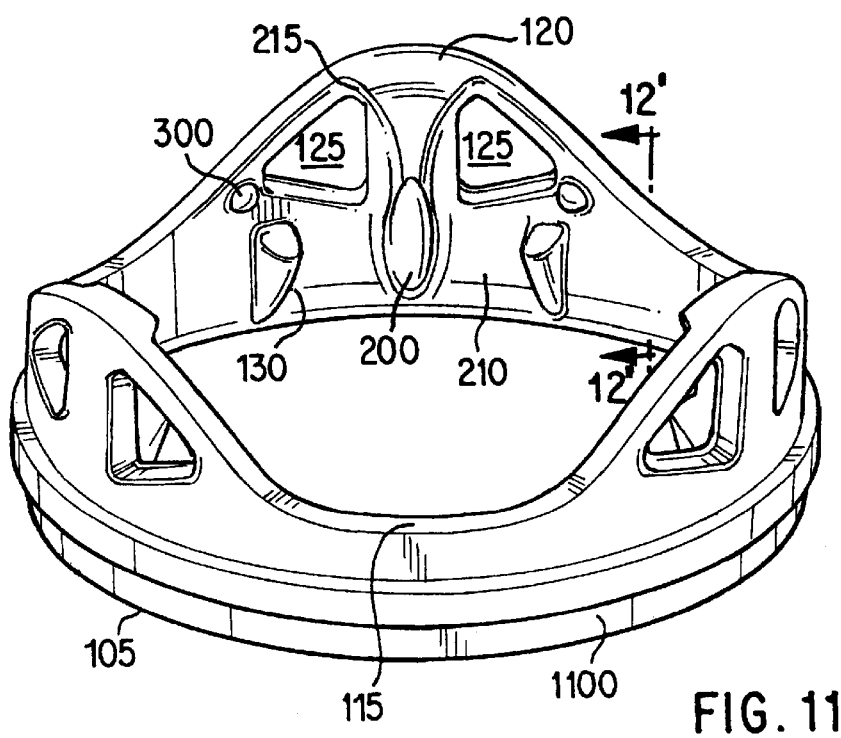
FIG. 11 is an isometric view of a preferred embodiment of a multi-leaflet mechanical heart valve according to the present invention with the leaflets removed.

FIG. 11 is an isometric view of a preferred embodiment of a multi-leaflet mechanical heart valve according to the present invention with the leaflets removed. As shown, each window 125 is placed just above a winglet guide path 210, the winglet guide path 210 being defined between an inflow projection 130 and a closing projection 200. Also shown in this figure is the sewing ring receiving portion 1100 of housing 105. Although in the preferred embodiment sewing ring receiving portion 1100 is an extended part of housing 105, other sewing ring attachment arrangements could be considered.

Figure 12:
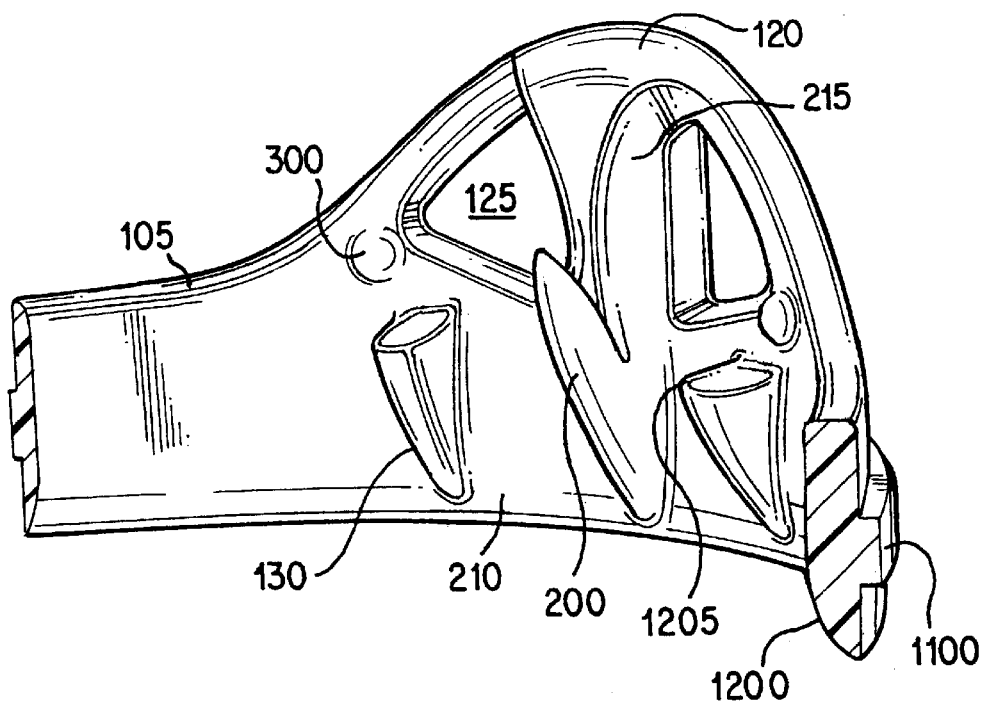
FIG. 12 is a partial cross-sectional isometric view taken along line 12'—12' in FIG. 11 of a preferred embodiment of a multi-leaflet mechanical heart valve according to the present invention with the leaflets removed.

FIG. 12 is a partial cross-sectional isometric view taken along line 12'—12' in FIG. 11 of a preferred embodiment of a multi-leaflet mechanical heart valve according to the present invention with the leaflets removed. As illustrated, inflow projection 130 includes a non-uniform surface portion 1205. I has been discovered through testing that additional wear resistance may be achieved through the use of this non-uniform, asymmetrical surface on one side of the inflow projection 130 as it mates with a complementary seating surface on each leaflet 110 (provides for surface interface contact rather than point interface contact).

Figure 13:
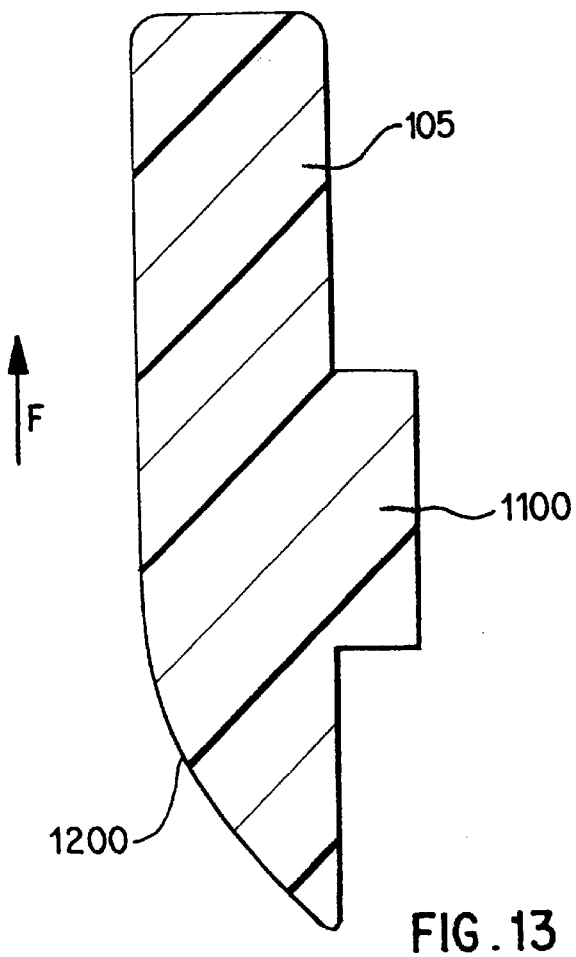
FIG. 13 is a cross-sectional plan view of the housing of a preferred embodiment of a multi-leaflet mechanical heart valve according to the present invention.

FIG. 13 is a cross-sectional plan view of the housing 105 of a preferred embodiment of a multi-leaflet mechanical heart valve according to the present invention. Although differing cross-sections could be considered, in the preferred embodiment, a converging nozzle cross-section is utilized. As shown, housing 105 of the preferred embodiment includes converging section 1200 as well as sewing ring receiving portion 1100. Thus, housing 105 of the preferred embodiment converges in the flow direction F which minimizes flow separation and turbulence on the inflow side of the valve during forward flow through the open valve. The converging nozzle also reduces the pressure drop or pressure gradient across the valve during forward flow through the open valve when compared to other heart valves which have a rather abrupt or blunt shape on the inflow side of the housing. Thus, the housing of the preferred embodiment has improved flow characteristics and minimizes pressure or energy losses and flow separation through the open valve.

Figure 14:
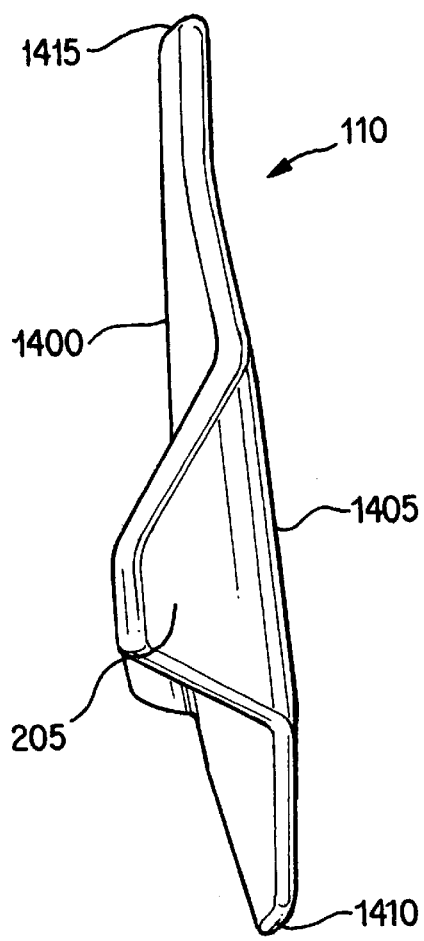
FIG. 14 is a side view of a preferred embodiment of a leaflet for a multi-leaflet mechanical heart valve according to the present invention.
Figure 15:
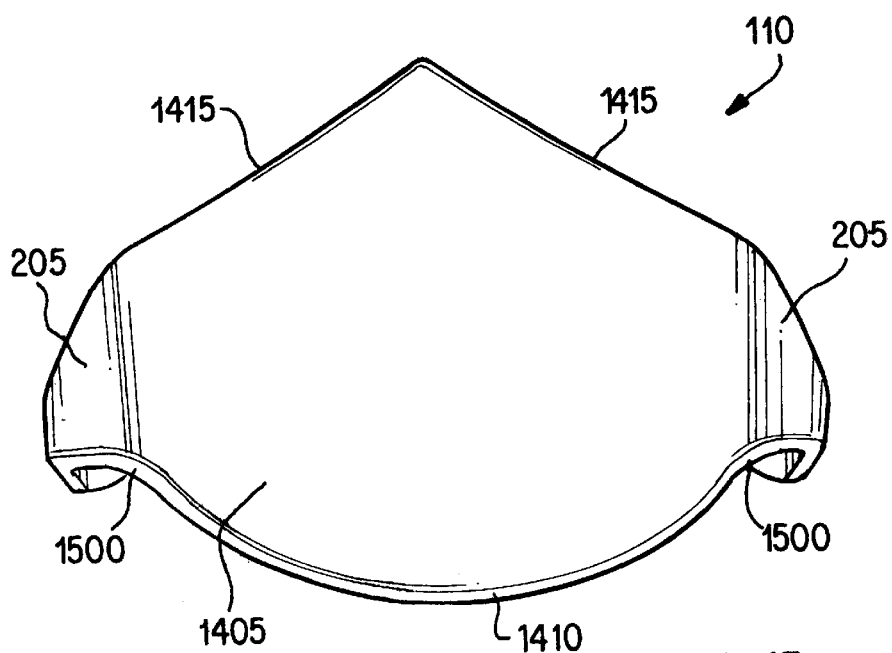
FIG. 15 is an isometric view of a preferred embodiment of a leaflet for a multi-leaflet mechanical heart valve according to the present invention.

FIG. 14 is a side view of a preferred embodiment of a leaflet 110 for a multi-leaflet mechanical heart valve according to the present invention. The preferred embodiment of the leaflet 110 according to the present invention includes a winglet 205 at each side of the main portion of the leaflet 110. FIG. 15 is an isometric view of a preferred embodiment of a leaflet 110 for a multi-leaflet mechanical heart valve according to the present invention. The main portion comprises inner flow surface 1400, outer flow surface 1405, leading edge surface 1410, and trailing edge surface 1415. As mentioned above, leaflet 110 includes two winglet seating portions 1500 which mate with inflow projections 130. As depicted in this figure, outer flow surface 1405 of leaflet 110 is concave along a line extending between the winglets 205.

Although the preferred embodiment of a leaflet 110 for a multi-leaflet mechanical heart valve according to the present invention is somewhat triangular in shape (because three leaflets are utilized), other shapes and numbers of leaflets may be utilized without departing from the scope or spirit of the present invention.

Figure 16:
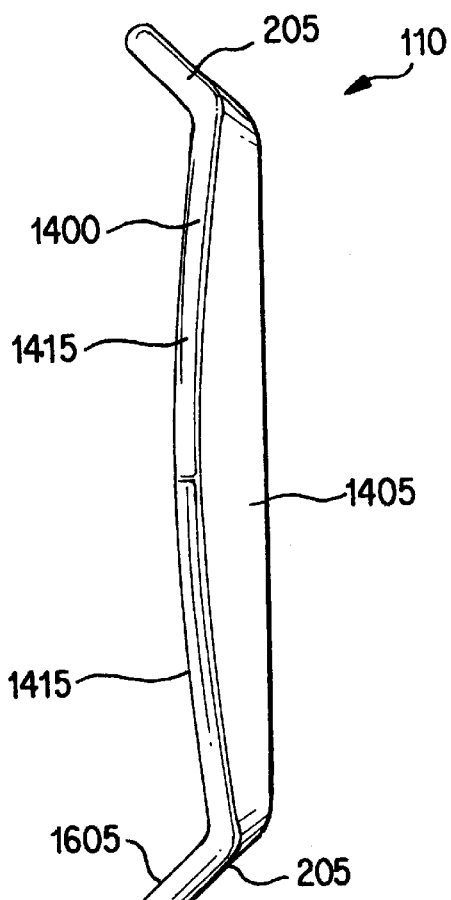
FIG. 16 is a front view of a preferred embodiment of a leaflet for a multi-leaflet mechanical heart valve according to the present invention.
Figure 17:
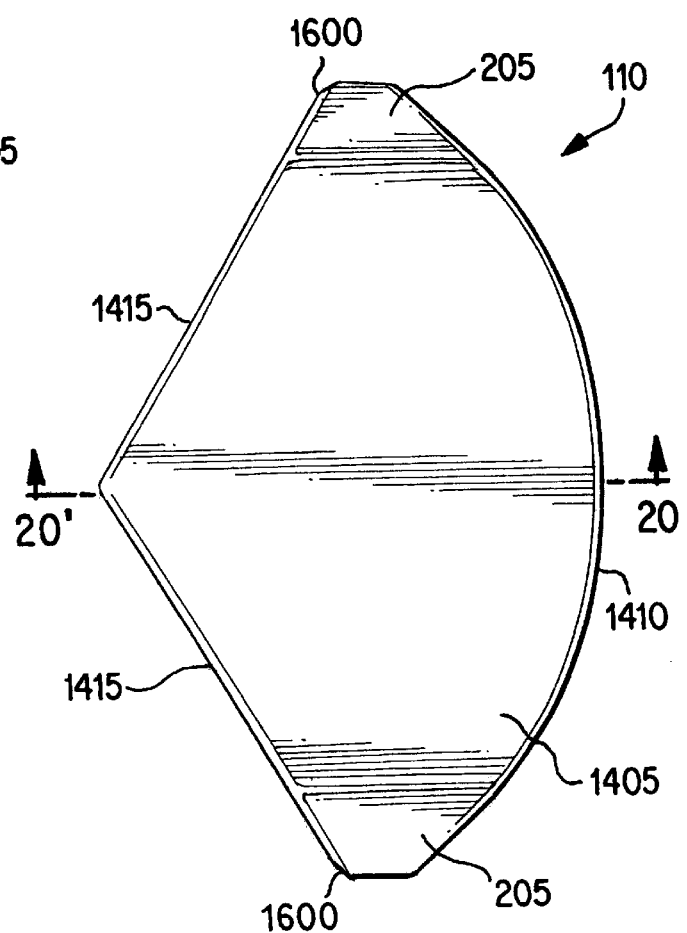
FIG. 17 is a top view of a preferred embodiment of a leaflet for a multi-leaflet mechanical heart valve according to the present invention.
Figure 18:
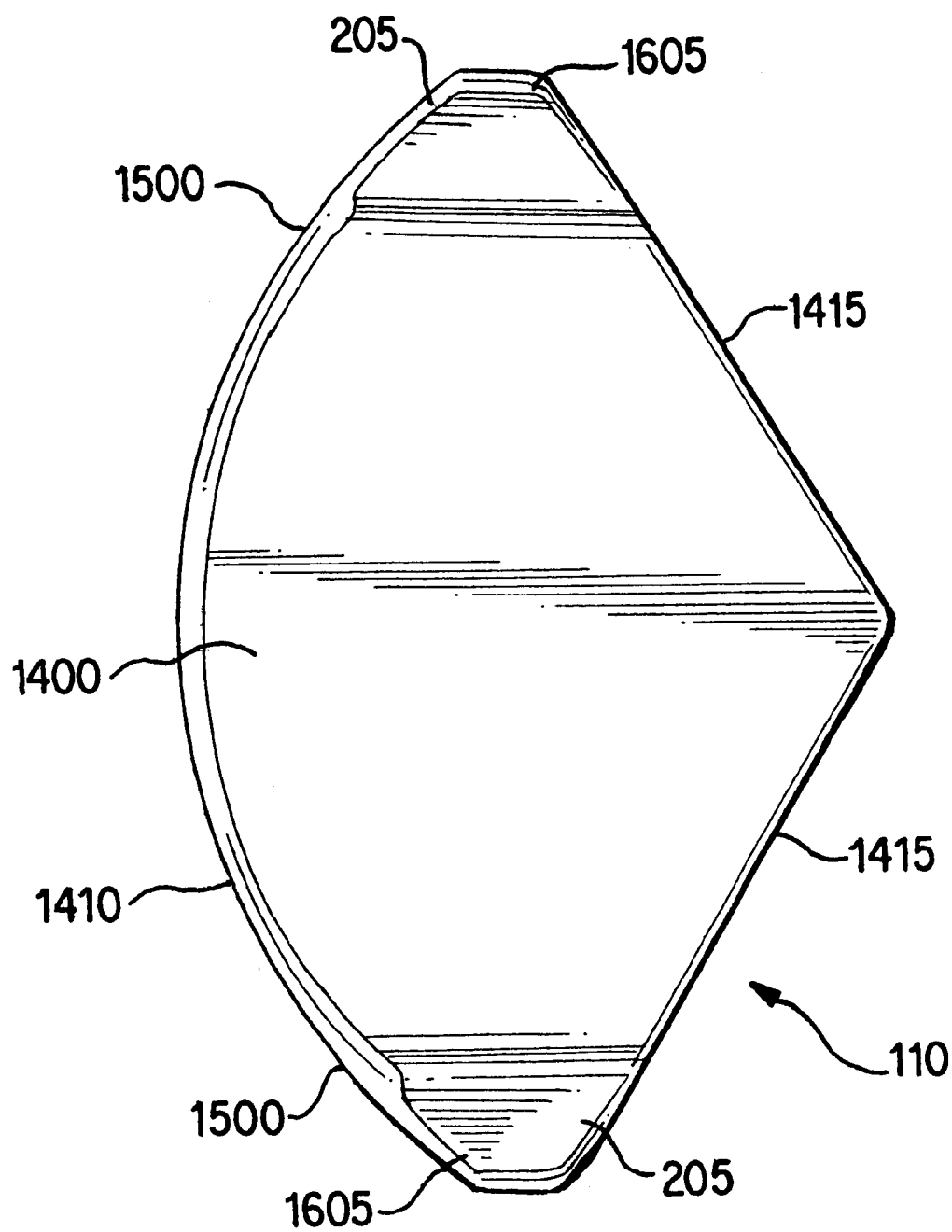
FIG. 18 is a bottom view of a preferred embodiment of a leaflet for a multi-leaflet mechanical heart valve according to the present invention.

FIG. 16 is a front view, FIG. 17 is a top view, and FIG. 18 is a bottom view of a preferred embodiment of a leaflet 110 for a multi-leaflet mechanical heart valve according to the present invention. As shown in these figures, winglets 205 include winglet outer surface 1600 and winglet inner surface 1605. Winglet outer surface 1600 is the surface that is washed by the blood flow through windows 125. As depicted in FIG. 18, inner flow surface 1400 of leaflet 110 is convex along a line extending between winglets 205.

Figure 19:
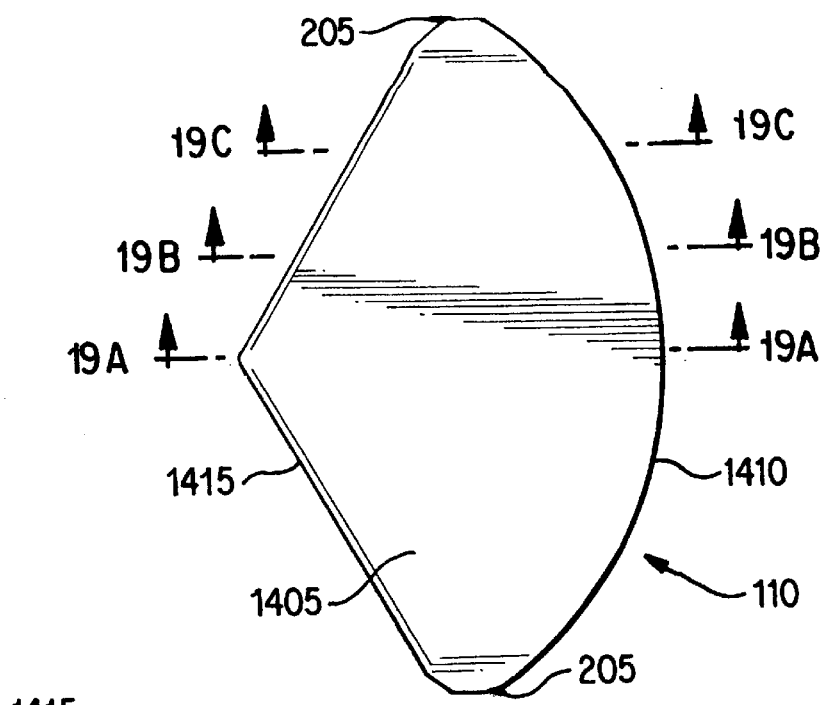
FIG. 19 is a top plan view of a preferred embodiment of a leaflet for a multi-leaflet mechanical heart valve according to the present invention with three differing cross sectional views included.
Figure 19A:
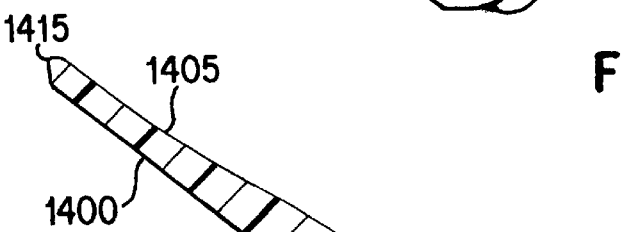
Figure 19B:
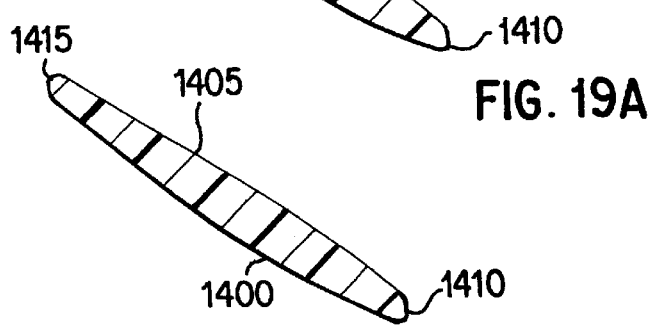
Figure 19C:
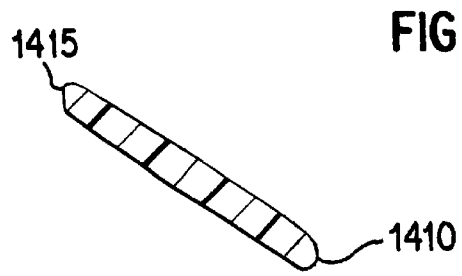

FIG. 19 is a top plan view of a preferred embodiment of a leaflet 110 for a multi-leaflet mechanical heart valve according to the present invention with three differing cross sectional views included. The section cuts (A, B, and C) show the changing cross section of the preferred embodiment of a leaflet 110 for a multi-leaflet mechanical heart valve according to the present invention from centerline A—A to just short of winglet 205. As can be seen, section A—A shows a cut of varying thicknesses and contours, and section C—C near the winglet 205 shows a cut with a lesser variation in thickness and less pronounced contours. Section B—B shows an intermediate cut exemplifying the transition between A—A and C—C. Preferably, the leaflet is symmetric about section A—A.

Figure 20:
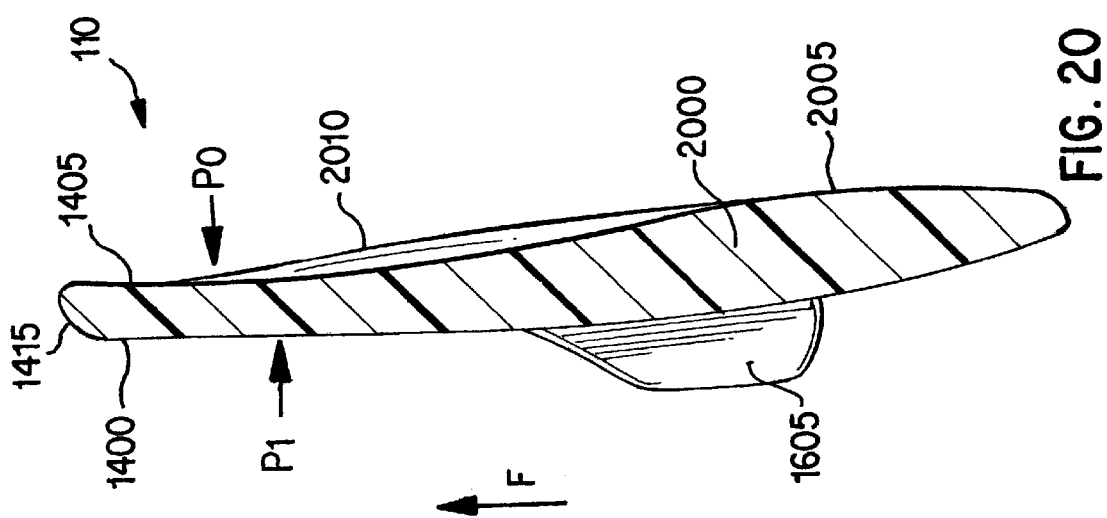
FIG. 20 is a cross-sectional view taken along line 20'—20' in FIG. 17 of the profile of a preferred embodiment of a leaflet for a multi-leaflet mechanical heart valve according to the present invention.

FIG. 20 is a cross-sectional view taken along line 20'—20' in FIG. 17 of the profile of a preferred embodiment of a leaflet 110 for a multi-leaflet mechanical heart valve according to the present invention. As shown, inner flow surface 1400 has a convex curvature from leading edge surface 1410 to trailing edge surface 1415. Outer flow surface 1405 has an S-shaped curvature from leading edge surface 1410 to trailing edge surface 1415. Outer flow surface 1405 has a convex curvature 2005 proximate the leading edge surface 1410. Furthermore, outer flow surface 1405 has a concave curvature 2010 proximate the trailing edge surface 1415.

The shape of the preferred embodiment of the leaflets 110 minimizes flow separation in the open position and enhances early closure of the leaflets. As will be appreciated by one skilled in the art of fluid mechanics, the shape of the leaflet 110 affects the pressure distribution over its surface as the blood flows over the around it. As shown in FIG. 20, leaflet 110 according to the present invention has an approximate virtual pivot axis at a location shown at 2000. Thus, during operation the pressure distribution over the leaflet will affect the rotational tendency of leaflet about the virtual pivot axis 2000.

Given the shape of the inner and outer flow surfaces, the differences between the static surface pressure along the inner flow surface $P_I$ and the outer flow surface $P_O$ and in view of the location of virtual pivot axis at a location shown approximately at 2000, the leaflet 110 is caused to tend towards rotation to a closed position. These pressure differentials are created by the airfoil-like shape of the leaflet 110 in the flow direction F. The fluid mechanics (including pressure gradients thereof during flow) of an airfoil are well known to those skilled in the fluid mechanics art. The early closure of the mechanical heart valve according to a preferred embodiment of the present invention starts as flow F through the valve 100 decelerates and the pressure field reverses. In the aortic position the leaflets 110 are substantially closed before the flow reverses, similar to the function of a natural aortic valve.

In another aspect, the inner and outer flow surfaces, 1400 and 1405, respectively, are advantageously designed such that in fully opened position of the leaflets the surface tangents of both flow surfaces at the trailing edge surface 1415 and the outer flow surface 1405 at the leading edge surface 1410 are substantially aligned in the direction of flow F to limit flow separation and eddy formation (turbulence) as blood flow leaves the trailing edge surface 1415 of the open leaflets 110. In accordance with a preferred embodiment of the present invention, the surface tangent of the inner flow surface 1400 proximate the leading edge surface 1410 of the leaflet 110 forms an angle of preferably about 0° to about 30° with respect to the flow direction. Thus, flow separation on both the inner and outer surfaces, 1400 and 1405, respectively, of the leaflet 110 is minimized. Accordingly the leaflets 110 of the mechanical heart valve 100 according to the present invention reduce turbulence, flow separation, and energy losses associated with flow through the open valve.

Figure 21:
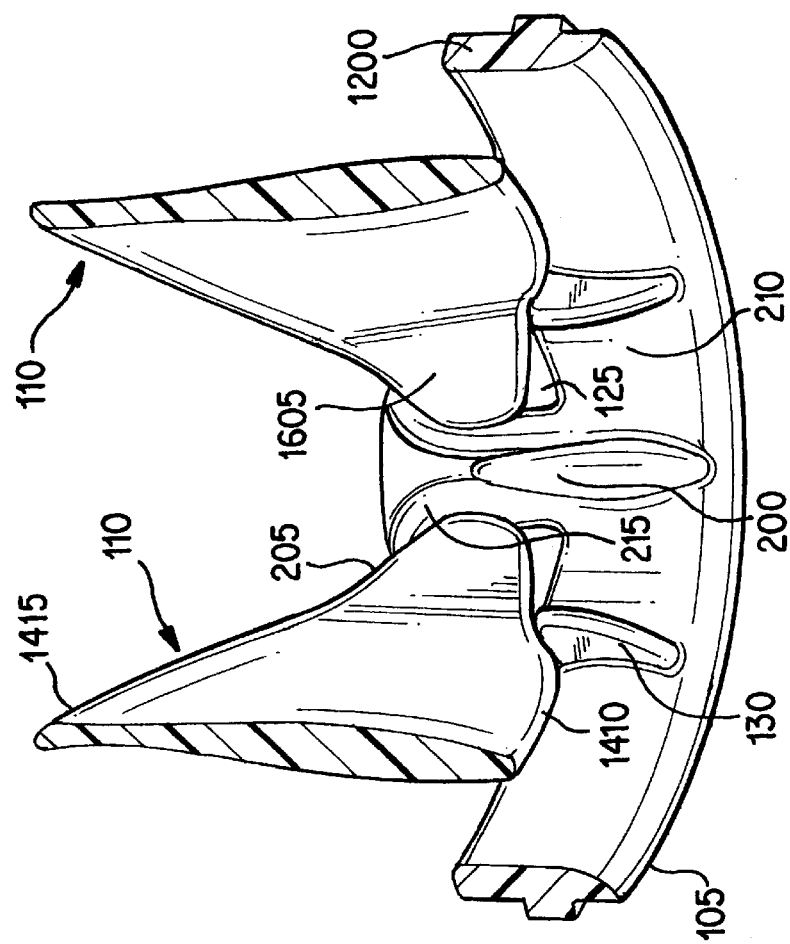
FIG. 21 is a cross-sectional view taken along line 21'—21' in FIG. 5 of a preferred embodiment of a multi-leaflet mechanical heart valve according to the present invention with the leaflets in the fully open position.

FIG. 21 is a cross-sectional view taken along line 21'—21' in FIG. 5 of a preferred embodiment of a multi-leaflet mechanical heart valve according to the present invention with the leaflets 110 in the fully open position. FIG. 21 clearly illustrates the interaction of winglets 205 with the winglet guide paths 210 and winglet guide arcs 215. Also, this figure shows that the distance between inflow projections 130 and the closing projection 200 decreases in the blood flow direction. Thus, winglet guide paths 210 create a nozzle effect to direct blood flow through windows 125 to substantially wash the rear surface of winglets 205 to minimize stagnation.

Figure 22:
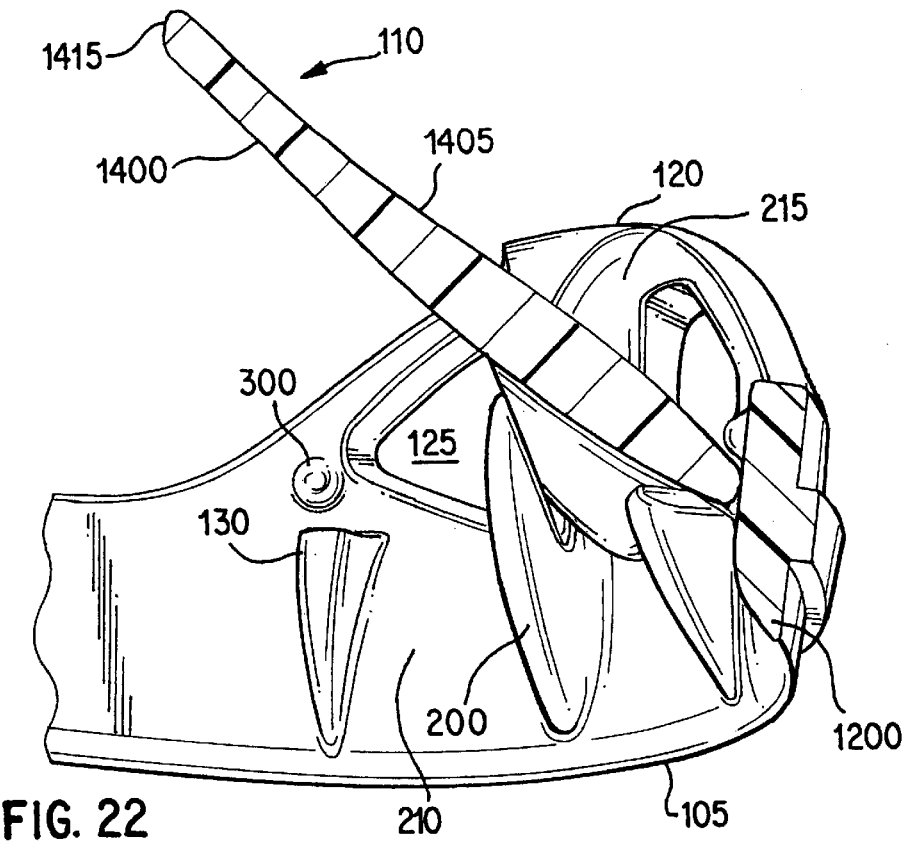
FIG. 22 is a cross-sectional view taken along line 22'—22' in FIG. 6 of a preferred embodiment of a multi-leaflet mechanical heart valve according to the present invention with only one of the leaflets which shown in the fully closed position.

FIG. 22 is a cross-sectional view taken along line 22'—22' in FIG. 6 of a preferred embodiment of a multi-leaflet mechanical heart valve according to the present invention with only one of the leaflets 110 shown in the fully closed position. As shown, when in the closed position, leaflet 110 rests upon inflow projections 130 and the closing projection 200. As also illustrated in this figure, leaflet capture projections 300 help to retain leaflet 110 in housing 105.

Figure 23:
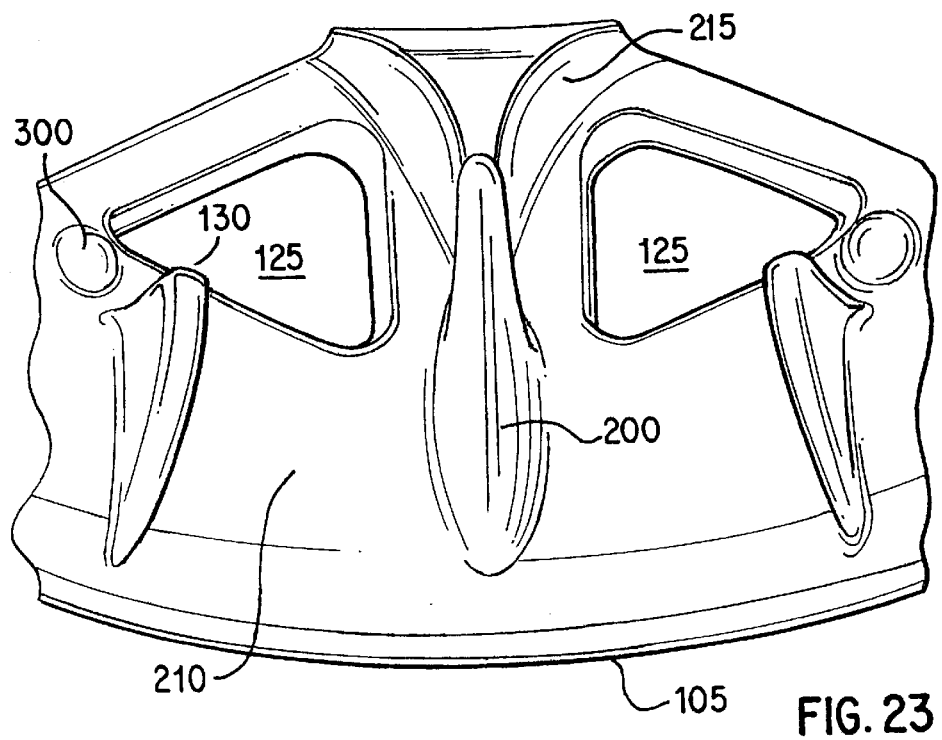
FIG. 23 is an enlarged cross-sectional view taken along line 21'—21' in FIG. 5 of a preferred embodiment of a multi-leaflet mechanical heart valve according to the present invention with the leaflets removed.

FIG. 23 is an enlarged cross-sectional view taken along line 21'—21' in FIG. 5 of a preferred embodiment of a multi-leaflet mechanical heart valve according to the present invention with the leaflets 110 removed. Like FIG. 21, this figure shows that the distance between inflow projections 130 and the closing projection 200 decreases in the blood flow direction due to the widening shape of the projections 130, 200. Thus, winglet guide paths 210 act as nozzles to direct blood flow through windows 125. This nozzle creates increased flow velocity into and around the windows 125 and winglet guide arcs 215. This figure also shows the aerodynamic and smoothed sculpting of inflow projections 130 and the closing projection 200 in the blood flow direction. These aerodynamic profiles help to limit flow separation and eddy formation (turbulence) as blood flows across these elements.

Figure 24A:
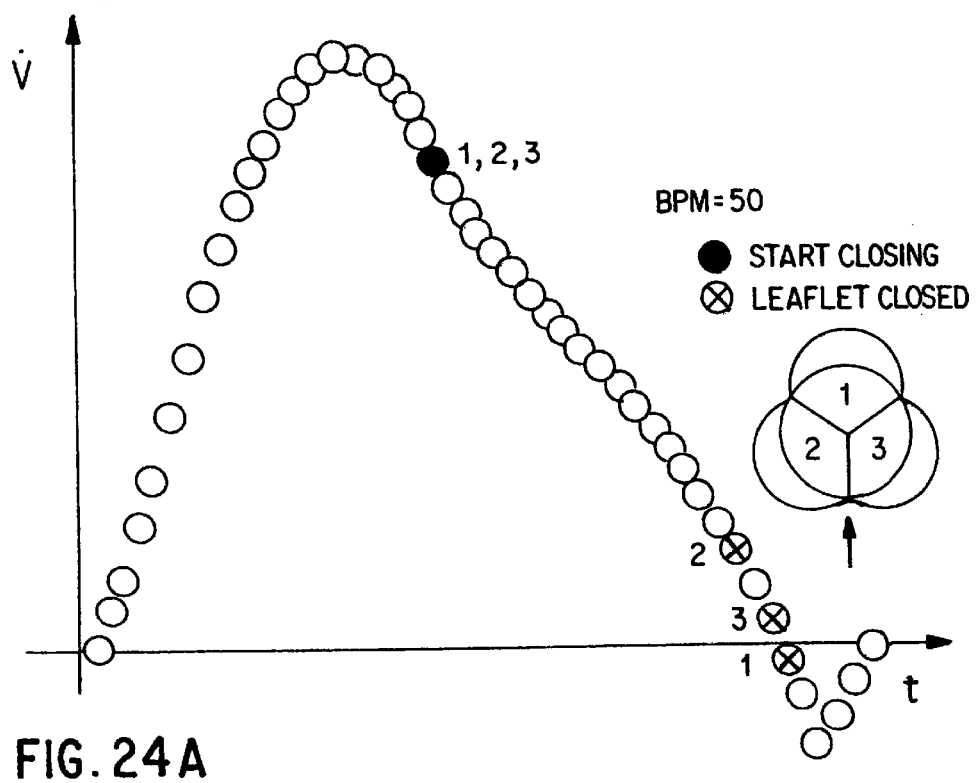
FIGS. 24(a), (b) and (c) are graphical representations of the performance of a preferred embodiment of a multi-leaflet mechanical heart valve according to the present invention in the aortic position at three differing heart rates, respectively.
Figure 24B:
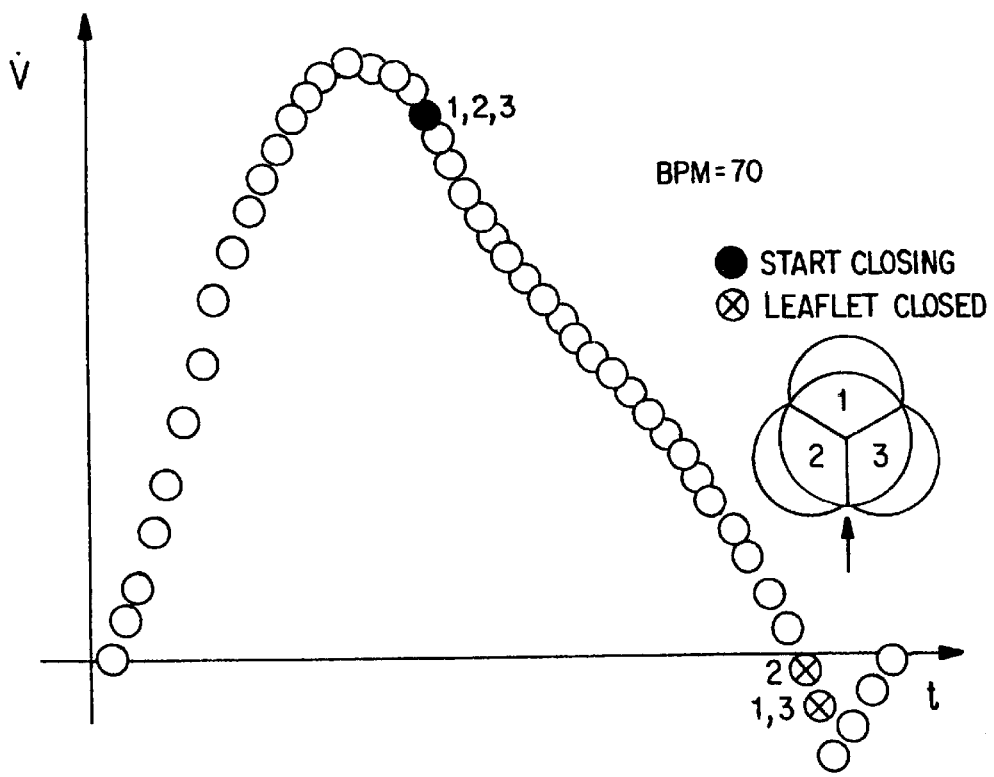
Figure 24C:
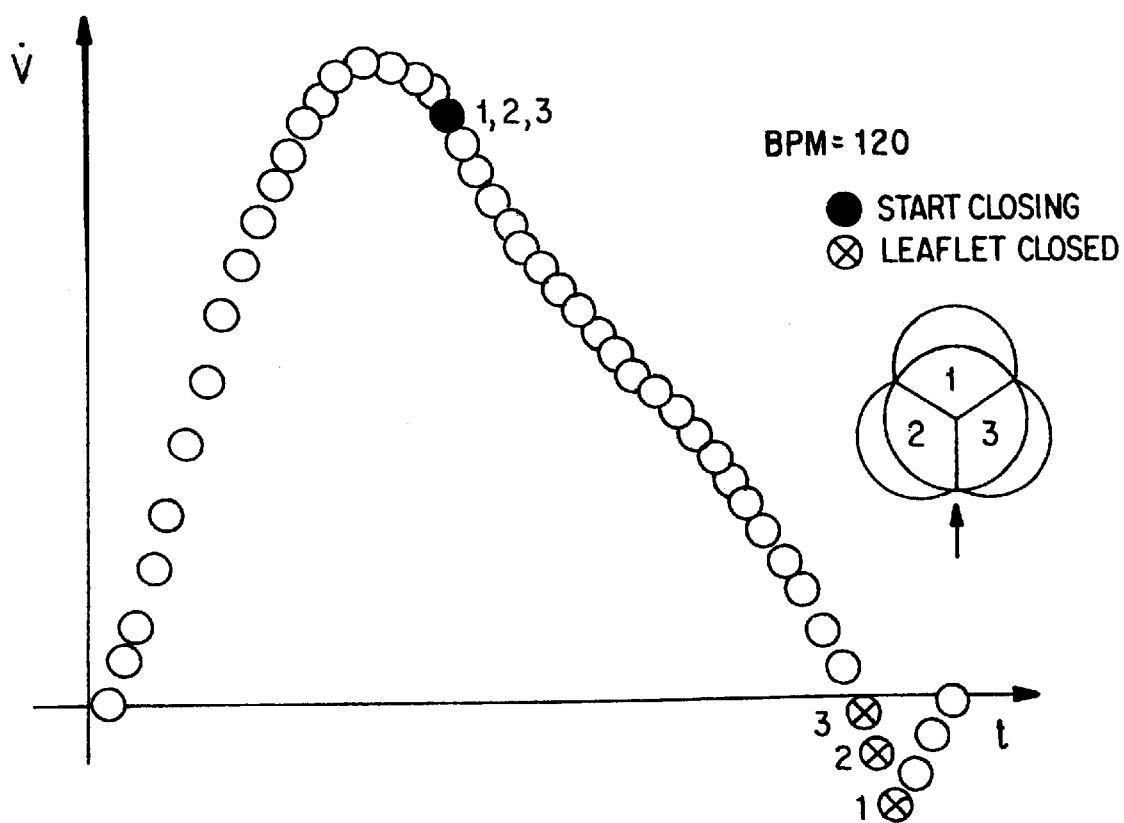
Figure 25A:
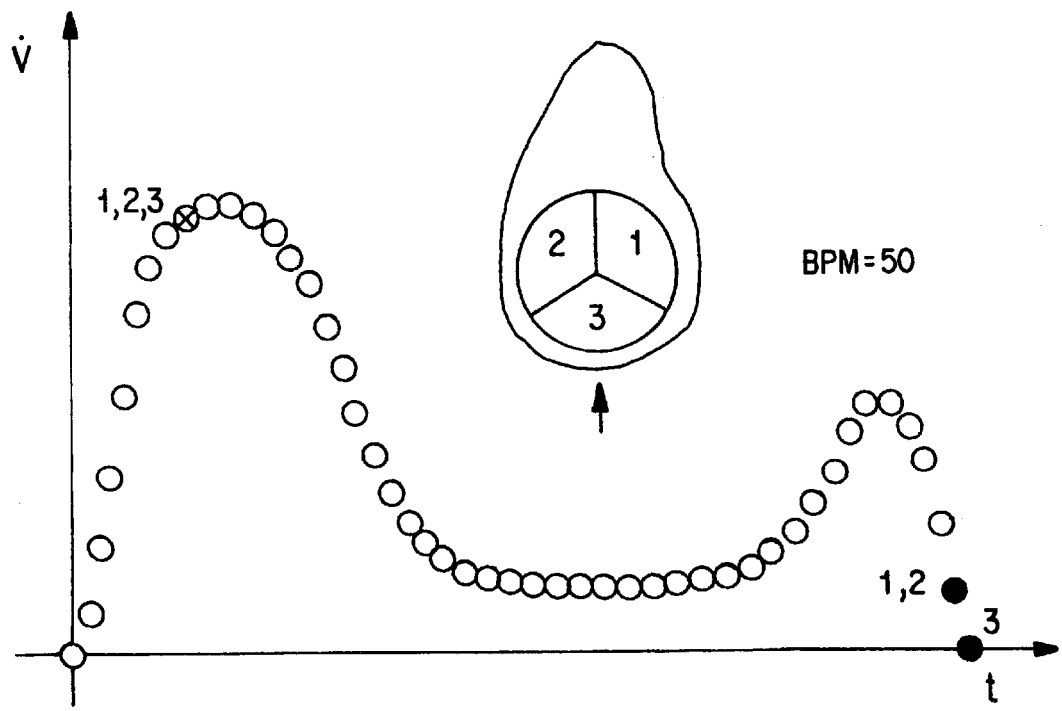
FIGS. 25(a), (b) and (c) are graphical representations of the performance of a preferred embodiment of a multi-leaflet mechanical heart valve according to the present invention in the mitral position at three differing heart rates, respectively.
Figure 25B:
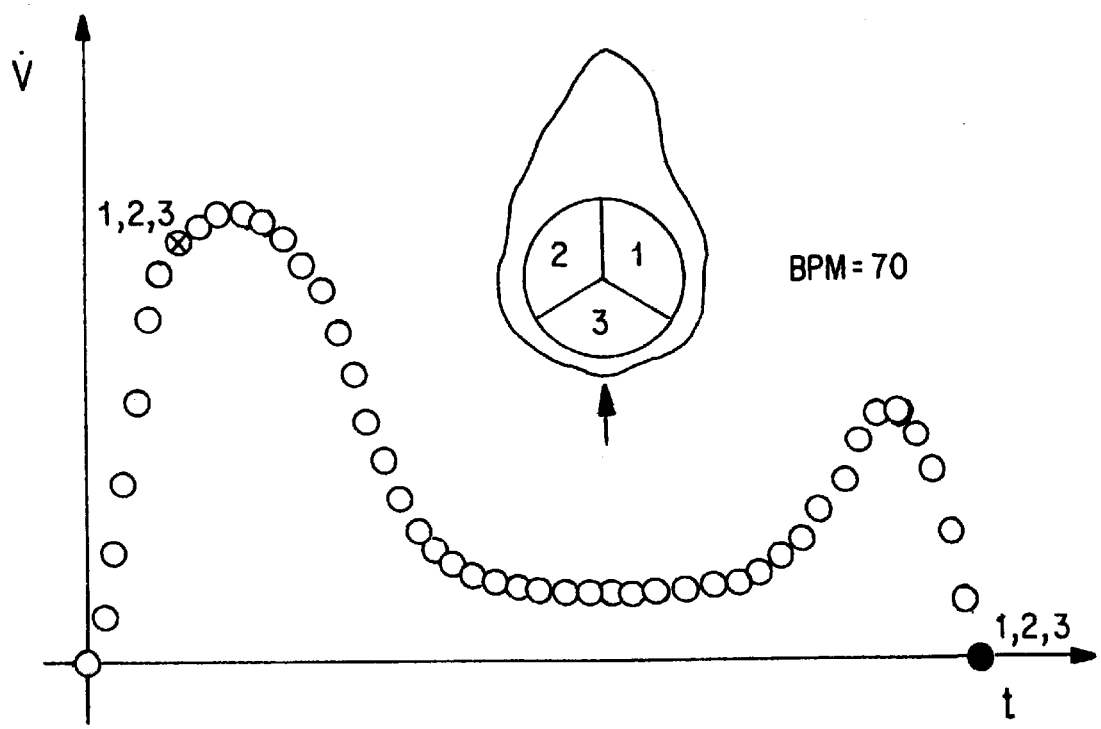
Figure 25C:
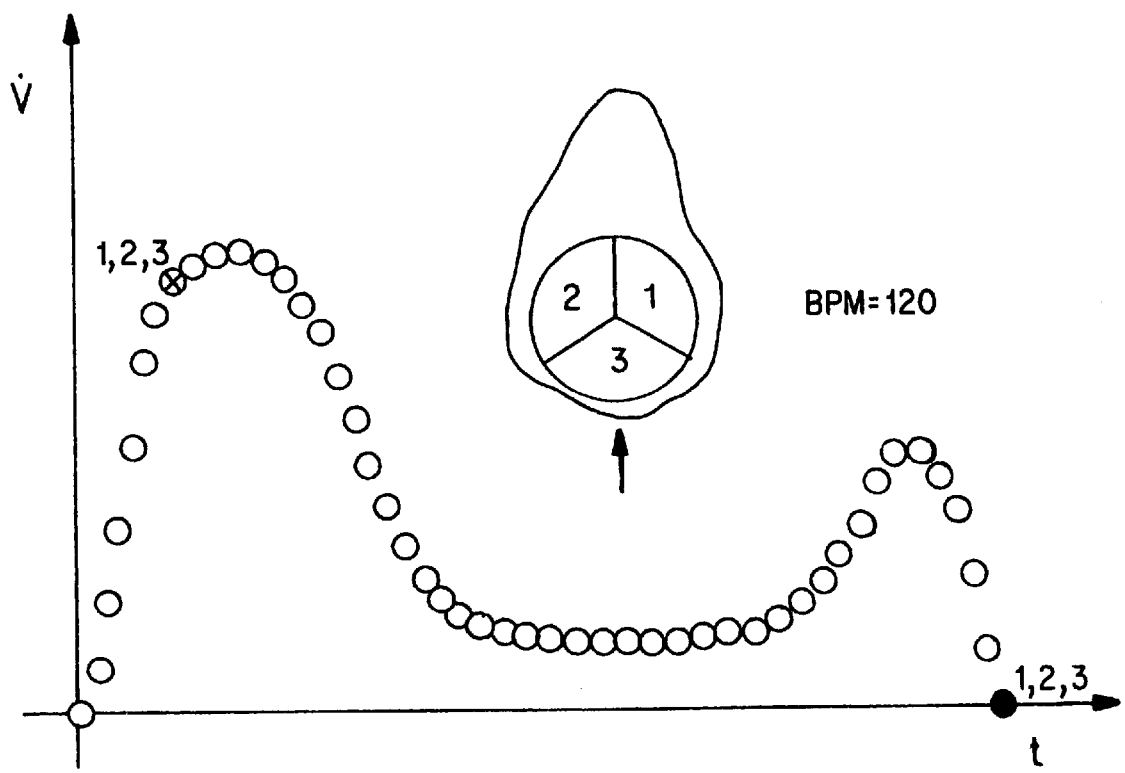

FIGS. 24 and 25 are graphical representations of the performance of a preferred embodiment of a multi-leaflet mechanical heart valve according to the present invention in the aortic and mitral positions respectively at three differing heart rates (50, 70, and 120 beats per minute). As shown in FIG. 24 in the aortic position, the preferred embodiment of a multi-leaflet mechanical heart valve according to the present invention begin to close very early. In fact, as illustrated, closure begins just after the flow peak (as flow decelerates and the pressure field reverses) and the valve the leaflets are substantially closed before the flow reverses (at V=0), similar to the function of a natural aortic valve. This early closure time is made possible by the flow characteristics of the preferred valve housing 105 as well as the preferred leaflets 110 which tend towards closure because of their novel geometry.

This closing behavior differs dramatically from that of conventional mechanical valve prostheses. As mentioned above, in conventional mechanical valve prostheses at the time when the flow rate becomes zero through the valve, conventional mechanical valve prostheses remain 90% open. Thus, with conventional mechanical valve prostheses, a significant portion of the closure (more than 90%) occurs during regurgitation (backward flow) of blood through the valve, and thus the closure is very rapid and entails a large amount of dynamic leakage (regurgitation). Thus, this very rapid closing under high pressure backward flow can lead to numerous undesirable results (cavitation, HITS, and unnecessary stress on the heart muscle). In contrast, the preferred embodiment of a multi-leaflet mechanical heart valve according to the present invention begins to close just after the flow peak (as flow decelerates and the pressure field reverses) and the valve's leaflets are substantially closed (approximately 90%) before the flow reverses (at V=0). Thus, the preferred embodiment of a multi-leaflet mechanical heart valve according to the present invention begins to close early and begins to close very slowly. Because the leaflets are almost completely closed prior to the initiation of the high pressure backward flow, the preferred embodiment of a multi-leaflet mechanical heart valve according to the present invention reduces the likelihood of cavitation, HITS, blood trauma, and regurgitation.

Of course, it should be understood that the closure performance of the present invention could be adjusted to meet desired criteria, such as a desired closing percentage at zero flow velocity (initiation of backwards flow), or timing of the initiation of closure rotation with respect to the maximum flow velocity. Preferable adjustments to the design could comprise modification of the airfoil-like geometry of the leaflets 110 to affect the pressure distributions along the inner and outer flow surfaces 1400 and 1405, respectively, a structural modification to the pivot structure to relocate the virtual pivot point of the leaflet, a reshaping of the leaflet to alter its center of mass or its neutral point, etc. The present invention conceives that optimal valve closure performance occurs between 50% to>90% closed before the flow reverses.

Figure 26:
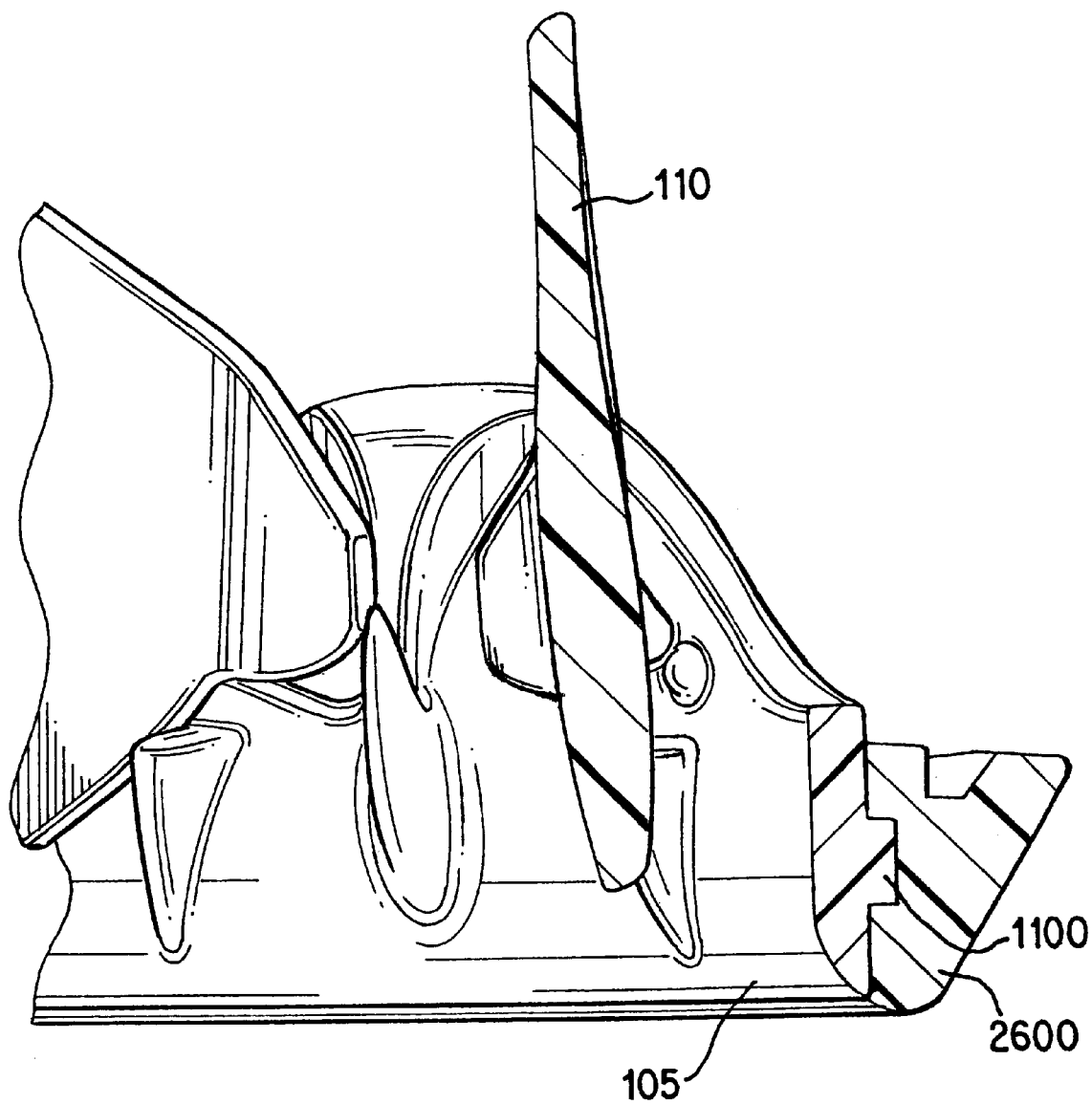
FIG. 26 is a a cross-sectional view similar to FIG. 21 which illustrates a preferred embodiment of a sewing ring for a multi-leaflet mechanical heart valve according to the present invention.

Finally, FIG. 26 is a a cross-sectional view similar to FIG. 21 which illustrates a preferred embodiment of a sewing ring for a multi-leaflet mechanical heart valve (in the aortic position) according to the present invention. As shown, this preferred sewing ring is attached to the outer circumference of housing 105 at sewing ring receiving portion 1100.

As illustrated in the detailed description, the improved mechanical heart valve for implantation into a patient in accordance with the present invention substantially eliminates one or more of the problems or disadvantages found in the prior art. The novel structure, as particularly pointed out in the written description and the appended drawings hereof, provides a improved mechanical heart valve for implantation into a patient which provides improved flow characteristics, minimizes blood clotting behind the leaflets, and provides more natural opening and closing behavior.

It will be apparent to those skilled in the art that various modifications and variations can be made in the mechanical heart valve for implantation into a patient of the present invention without departing from the spirit or scope of the invention. Thus, it is intended that the present invention cover the modifications and variations of this invention provided they come within the scope of the disclosure hereof and any equivalents of the structures disclosed herein.

We claim:

1. A rotatable leaflet for a prosthetic heart valve comprising:
    a main portion including leading and trailing edge surfaces, and inner and outer surfaces connecting the leading and trailing edge surfaces, wherein the inner surface generally defines a convex curvature from the leading edge surface to the trailing edge surface and the outer surface generally defines a convex curvature proximate the leading edge surface and a concave curvature proximate the trailing edge surface; and
    first and second winglet portions situated on opposite ends of the leaflet to facilitate rotation of the leaflet.

2. The rotatable leaflet of claim 1, wherein the inner surface has a convex curvature from the first winglet portion to the second winglet portion.

3. The rotatable leaflet of claim 1, wherein the outer surface has a concave curvature from the first winglet portion to the second winglet portion.

4. The rotatable leaflet of claim 1, 2, or 3, wherein the distance between the inner and outer surfaces is greater proximate the leading edge surface than the distance between the inner and outer surfaces proximate the trailing edge surface such that the leaflet has an airfoil-like cross section.

5. The rotatable leaflet of claim 4, wherein the leaflet is formed from pyrolytic carbon.

6. The rotatable leaflet of claim 1, wherein the leaflet is formed from pyrolytic carbon.

7. The rotatable leaflet of claim 1, wherein each winglet portion is attached to the inner and outer surfaces and the leading and trailing edge surfaces.

8. A rotatable leaflet for an early-closing prosthetic heart valve comprising:
    a main portion including leading and trailing edge surfaces, and inner and outer surfaces connecting the leading and trailing edge surfaces;
    first and second winglet portions situated on opposite ends of the leaflet to facilitate rotation of the leaflet; and
    closure means for causing the leaflet to rotate toward a closed position prior to substantial backwards flow of blood through the heart valve.

9. The rotatable leaflet of claim 8, wherein the closure means causes the leaflet to begin to rotate toward a closed position about when a maximum flow rate has been achieved through the valve.

10. The rotatable leaflet of claim 8, wherein the closure means comprises a configuration wherein the inner surface has a convex curvature from the leading edge surface to the trailing edge surface and the outer surface has a convex curvature proximate the leading edge surface and a concave curvature proximate the trailing edge surface.

11. The rotatable leaflet of claim 10, wherein the closure means further comprises a configuration wherein the distance between the inner and outer surfaces is greater proximate the leading edge surface than the distance between the inner and outer surfaces proximate the trailing edge surface such that the leaflet has an airfoil-like cross section.

12. The rotatable leaflet of claim 10, wherein the inner surface has a convex curvature from the first winglet portion to the second winglet portion.

13. The rotatable leaflet of claim 12, wherein the outer surface has a concave curvature from the first winglet portion to the second winglet portion.

14. The rotatable leaflet of claim 8 or 11, wherein the leaflet is formed from pyrolytic carbon.

15. A mechanical prosthetic heart valve, the valve comprising:
    an annular housing having an inner circumferential surface; and
    at least one leaflet disposed adjacent to the inner circumferential surface and capable of rotation between an open position in which blood can flow through the heart valve and a closed position in which blood is prevented from flowing through the heart valve, the leaflet comprising:
        a main portion including leading and trailing edge surfaces, and inner and outer surfaces connecting the leading and trailing edge surfaces, wherein the inner surface generally defines a convex curvature from the leading edge surface to the trailing edge surface and the outer surface generally defines a convex curvature proximate the leading edge surface and a concave curvature proximate the trailing edge surface; and
        first and second winglet portions situated on opposite ends of the leaflet to facilitate rotation of the leaflet.

16. The mechanical prosthetic heart valve of claim 15, wherein the annular housing comprises a nozzle shape along the inner circumferential surface.

17. The mechanical prosthetic heart valve of claim 15, wherein the inner circumferential surface includes inflow projections to receive the leaflet.

18. The mechanical prosthetic heart valve of claim 15, wherein the inner surface of the at least one leaflet has a convex curvature from the first winglet portion to the second winglet portion.

19. The mechanical prosthetic heart valve of claim 18, wherein the outer surface of the at least one leaflet has a concave curvature from the first winglet portion to the second winglet portion.

20. The mechanical prosthetic heart valve of claim 15, 18 or 19, wherein the distance between the inner and outer surfaces of the at least one leaflet is greater proximate the leading edge surface than the distance between the inner and outer surfaces proximate the trailing edge surface such that the at least one leaflet has an airfoil-like cross section.

21. The mechanical prosthetic heart valve of claim 15, further comprising at least two leaflets.

22. The mechanical prosthetic heart valve of claim 21, further comprising at least three leaflets.

23. The mechanical prosthetic heart valve of claim 15, wherein the valve housing is formed from a metallic material.

24. The mechanical prosthetic heart valve of claim 15, wherein the at least one leaflet is formed from pyrolytic carbon.

25. A mechanical early-closing prosthetic heart valve, the valve comprising:
an annular housing having an inner circumferential surface; and
at least one leaflet disposed adjacent to the inner circumferential surface and capable of rotation between an open position in which blood can flow through the heart valve and a closed position in which blood is prevented from flowing through the heart valve, the leaflet comprising closure means for causing the leaflet to rotate toward a closed position prior to substantial back flow of blood through the heart valve.

26. The mechanical early-closing prosthetic heart valve of claim 25, wherein the closure means causes the leaflet to begin to rotate toward a closed position about when a maximum flow rate has been achieved through the valve.

27. The mechanical early-closing prosthetic heart valve of claim 25, wherein the at least one leaflet comprises:
a main portion including leading and trailing edge surfaces, and inner and outer surfaces connecting the leading and trailing edge surfaces; and
first and second winglet portions situated on opposite ends of the at least one leaflet to facilitate rotation of the leaflet.

28. The mechanical early-closing prosthetic heart valve of claim 27, wherein the closure means comprises a configuration wherein the inner surface generally defines a convex curvature from the leading edge surface to the trailing edge surface and the outer surface generally defines a convex curvature proximate the leading edge surface and a concave curvature proximate the trailing edge surface.

29. The mechanical early-closing prosthetic heart valve of claim 28, wherein the closure means further comprises a configuration wherein the distance between the inner and outer surfaces of the at least one leaflet is greater proximate the leading edge surface than the distance between the inner and outer surfaces proximate the trailing edge surface such that the leaflet has an airfoil-like cross section.

30. A mechanical prosthetic heart valve comprising:
an annular housing having an inner circumferential surface; and
at least one leaflet disposed adjacent to the inner circumferential surface and capable of rotation between an open position in which blood can flow through the heart valve and a closed position in which blood is prevented from flowing through the heart valve, the at least one leaflet comprising a main portion including leading and trailing edge surfaces, and inner and outer surfaces connecting the leading and trailing edge surfaces, and first and second winglet portions situated on opposite ends of the at least one leaflet to facilitate rotation of the at least one leaflet; and
first and second leaflet pivot structures adapted to cooperate with the first and second winglets, respectively, to facilitate rotation of the at least one leaflet between the open and closed positions, each of the first and second leaflet pivot structures comprising:
an inflow projection extending from the inner circumferential surface of the housing and adapted to contact one of the winglet portions in one of the open and closed positions; and
a closing projection extending from the inner circumferential surface of the housing and adapted to contact one of the winglet portions in the closed position, wherein the closing projection and the inflow projection are configured and spaced from one another to increase flow velocity proximate the one of the winglet portions.

31. The mechanical prosthetic heart valve of claim 30, wherein each inflow projection has a first width proximate the inner surface of the annular housing, and a second width distal from the inner surface of the valve housing less than the first width.

32. The mechanical prosthetic heart valve of claim 30, wherein each closing projection has a first width proximate the inner surface of the annular housing, and a second width distal from the inner surface of the valve housing less than the first width.

33. The mechanical prosthetic heart valve of claim 30, wherein the annular housing defines at least one opening therethrough proximate the inflow and closing projections.

34. The mechanical prosthetic heart valve of claim 33, wherein the distance between the inflow projection and the closing projection decreases in the blood flow direction to direct at least a portion of the blood flow through the at least one opening when the at least one leaflet is in the open position.

35. The mechanical prosthetic heart valve of claim 30, wherein the inner surface of the at least one leaflet generally defines a convex curvature from the leading edge surface to the trailing edge surface and the outer surface of the at least one leaflet generally defines a convex curvature proximate the leading edge surface and a concave curvature proximate the trailing edge surface.

36. The mechanical prosthetic heart valve of claim 35, wherein the distance between the inner and outer surfaces is greater proximate the leading edge surface than the distance between the inner and outer surfaces proximate the trailing edge surface such that the at least one leaflet has an airfoil-like cross section.

37. A mechanical prosthetic heart valve comprising:
an annular housing having an inner circumferential surface and defining at least one opening through the circumferential surface; and
at least one leaflet disposed adjacent to the inner circumferential surface and capable of rotation between an open position in which blood can flow through the heart valve and a closed position in which blood is prevented from flowing through the heart valve, the at least one leaflet comprising a main portion and first and second winglet portions situated on opposite ends of the leaflet to facilitate rotation of the leaflet, wherein no portion of the at least one leaflet is received within the at least one opening during rotation between the open and the closed position to provide for increased blood flow proximate to one of the winglet portions.

38. The mechanical prosthetic heart valve of claim 37, wherein the annular housing includes first and second leaflet pivot structures adapted to cooperate with the first and second winglet portions, respectively, to facilitate rotation of the at least one leaflet between the open and closed positions, each of the first and second leaflet pivot structures comprising:
  an inflow projection extending from the inner circumferential surface of the housing and adapted to contact one of the winglet portions in one of the open and closed positions; and
  a closing projection extending from the inner circumferential surface of the housing and adapted to contact one of the winglet portions in the closed position, wherein the closing projection and the inflow projection are configured and spaced from one another to direct flow through the at least one opening through the circumferential surface.

39. The mechanical prosthetic heart valve of claim 38, wherein the at least one opening through the circumferential surface is proximate the opening and closing projections.

40. The mechanical prosthetic heart valve of claim 37, wherein the main portion of the at least one leaflet includes leading and trailing edge surfaces, and inner and outer surfaces connecting the leading and trailing edge surfaces, and wherein the inner surface generally defines a convex curvature from the leading edge surface to the trailing edge surface and the outer surface generally defines a convex curvature proximate the leading edge surface and a concave curvature proximate the trailing edge surface.

41. The mechanical prosthetic heart valve of claim 40 wherein the distance between the inner and outer surfaces is greater proximate the leading edge surface than the distance between the inner and outer surfaces proximate the trailing edge surface such that the at least one leaflet has an airfoil cross section.

42. The mechanical prosthetic heart valve of claim 37, wherein the annular housing is formed from a metallic material.

43. The mechanical prosthetic heart valve of claim 37, wherein the at least one leaflet is formed from pyrolytic carbon.

44. A mechanical early-closing prosthetic heart valve, the valve comprising:
  an annular housing having an inner circumferential surface; and
  at least one leaflet disposed adjacent to the inner circumferential surface and capable of rotation between an open position in which blood can flow through the heart valve and a closed position in which blood is prevented from flowing through the heart valve, the at least one leaflet comprising an early-closure means for creating a tendency for the leaflet to rotate toward the closed position such that the leaflet is substantially closed prior to initiation of back flow of blood through the heart valve.

45. The mechanical early-closing prosthetic heart valve of claim 44, whereby the at least one leaflet is more than 50% closed prior to the initiation of back flow of blood through the heart valve.

46. The mechanical early-closing prosthetic heart valve of claim 45, whereby the at least one leaflet is more than 60% closed prior to the initiation of back flow of blood through the heart valve.

47. The mechanical early-closing prosthetic heart valve of claim 46, whereby the at least one leaflet is more than 70% closed prior to the initiation of back flow of blood through the heart valve.

48. The mechanical early-closing prosthetic heart valve of claim 47, whereby the at least one leaflet is more than 80% closed prior to the initiation of back flow of blood through the heart valve.

49. The mechanical early-closing prosthetic heart valve of claim 48, whereby the at least one leaflet is more than 90% closed prior to the initiation of back flow of blood through the heart valve.

50. The mechanical early-closing prosthetic heart valve of claim 46, wherein the at least one leaflet further comprises:
  a main portion including leading and trailing edge surfaces, and inner and outer surfaces connecting the leading and trailing edge surfaces; and
  first and second winglet portions situated on opposite ends of the at least one leaflet to facilitate rotation of the at least one leaflet, each of the winglet portions having a first side proximate the annular housing and a second side opposite thereto.

51. The mechanical early-closing prosthetic heart valve of claim 50, wherein the early-closure means comprises a configuration wherein the inner surface of the at least one leaflet has a convex curvature from the leading edge surface to the trailing edge surface and the outer surface has a convex curvature proximate the leading edge surface and a concave curvature proximate the trailing edge surface.

52. The mechanical early-closing prosthetic heart valve of claim 51, wherein the early-closure means comprises a configuration wherein the distance between the inner and outer surfaces of the at least one leaflet is greater proximate the leading edge surface than the distance between the inner and outer surfaces proximate the trailing edge surface such that the at least one leaflet has an airfoil cross section.

53. The mechanical early-closing prosthetic heart valve of claim 50, wherein at least one opening through the annular housing is provided to allow blood flow across the first side of at least one of the winglet portions when the at least one leaflet is in the open position.

54. A mechanical early-closing prosthetic heart valve, the valve comprising:
  an annular housing having an inner circumferential surface; and
  at least one leaflet disposed adjacent to the inner circumferential surface and capable of rotation between an open position in which blood can flow through the heart valve and a closed position in which blood is prevented from flowing through the heart valve, the at least one leaflet comprising surfaces with complex curvatures and means for creating a tendency for the at least one leaflet to rotate toward the closed position such that the at least one leaflet is substantially closed prior to the initiation of back flow of blood through the heart valve.

55. The mechanical early-closing prosthetic heart valve of claim 54, wherein the surfaces with complex curvatures causes the at least one leaflet to begin to rotate toward a closed position about when a maximum flow rate has been achieved through the valve.

56. The mechanical early-closing prosthetic heart valve of claim 54, wherein the at least one leaflet further comprises:
- a main portion including leading and trailing edge surfaces, and inner and outer surfaces connecting the leading and trailing edge surfaces; and
- first and second winglet portions situated on opposite ends of the at least one leaflet to facilitate rotation of the at least one leaflet, each of the winglet portions having a first side proximate the annular housing and a second side opposite thereto.

57. The mechanical early-closing prosthetic heart valve of claim 56, wherein the complex curvatures comprise a configuration wherein the inner surface of the at least one leaflet has a convex curvature from the leading edge surface to the trailing edge surface and the outer surface has a convex curvature proximate the leading edge surface and a concave curvature proximate the trailing edge surface.

58. The mechanical early-closing prosthetic heart valve of claim 57, wherein the complex curvatures comprise a configuration wherein the distance between the inner and outer surfaces of the at least one leaflet is greater proximate the leading edge surface than the distance between the inner and outer surfaces proximate the trailing edge surface such that the at least one leaflet has an airfoil cross section.

59. The mechanical early-closing prosthetic heart valve of claim 56, wherein at least one opening through the inner circumferential surface is provided to allow blood flow across the first side of at least one of the winglet portions when the at least one leaflet is in the open position.

* * * * *